(12) United States Patent
Alig et al.

(10) Patent No.: US 6,506,744 B1
(45) Date of Patent: Jan. 14, 2003

(54) BENZAZEPINONE-DERIVATIVES

(75) Inventors: Leo Alig, Magden (CH); Alexander Chucholowski, Grenzach-Wyhlen (DE); Thomas Weller, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/611,700

(22) Filed: Jul. 7, 2000

(30) Foreign Application Priority Data

Jul. 13, 1999 (EP) ............................................ 99113708

(51) Int. Cl.[7] .................. C07D 239/96; C07D 243/12; C07D 265/22; A61K 31/517; A61K 31/553
(52) U.S. Cl. .................................. 514/211.05; 540/490
(58) Field of Search ...................... 540/490; 514/211.05

(56) References Cited

U.S. PATENT DOCUMENTS

| 5,250,679 A | 10/1993 | Blackburn et al. ............. 261/14 |
| 5,705,890 A | 1/1998 | Blackburn et al. .......... 314/220 |
| 5,877,278 A | 3/1999 | Zuckermann et al. ....... 530/334 |
| 6,100,282 A | 8/2000 | Alig et al. .................. 514/371 |

FOREIGN PATENT DOCUMENTS

| EP | 566 018 | 10/1993 |
| EP | A 98100006.0 | 1/1998 |
| EP | A 99113708.4 | 7/1999 |
| WO | 93/00095 | 1/1993 |
| WO | 97/24119 | 7/1997 |
| WO | 98/04247 | 2/1998 |
| WO | 98/46576 | 10/1998 |

OTHER PUBLICATIONS

Süsse et al., Monatshefte. Chemie, 118, p. 71–79 (1987).
Blackburn et al., J. Med. Chem., 40, p. 717–729 (1997).
G. M. Coppola, J. Heterocyclic Chem., 23, p. 223–227 (1986).
Andrea et al., J. Org. Chem., 56, p. 3133–3137 (1991).
Liu et al., Synlett, p. 1037–1039 (1995).
Ohba et al., Chem. Pharm. Bull., 40, p. 2543–2546 (1992).
M. Peerzada, Org. Prep. Proceed. Int., 17, p. 267–270 (1985).
Fryer et al., J. Heterocyclic Chem., 28, p. 1203–1208 (1991).

*Primary Examiner*—Bruck Kifle
(74) *Attorney, Agent, or Firm*—George W. Johnston; Patricia S. Rocha-Tramaloni

(57) ABSTRACT

Compounds of formula I

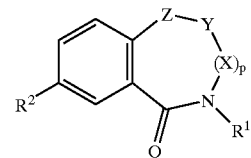

as well as pharmaceutically usable salts and esters thereof, inhibit the binding of adhesive proteins to the surface of different types of cell and accordingly influence cell-cell and cell-matrix interactions. They can be used in the form of pharmaceutical preparations for the treatment or prevention of neoplasms, tumor metastasis, tumor growth, osteoporosis, Paget's disease, diabetic retinopathy, macular degeneration, restenosis following vascular intervention, psoriasis, arthritis, fibrosis, kidney failure as well as infection caused by viruses, bacteria or fungi.

30 Claims, No Drawings

BENZAZEPINONE-DERIVATIVES

SUMMARY OF THE INVENTION

The invention is concerned especially with benzazepinone derivatives of formula I

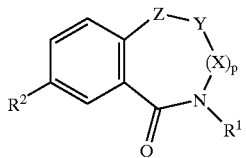

wherein

R¹ is

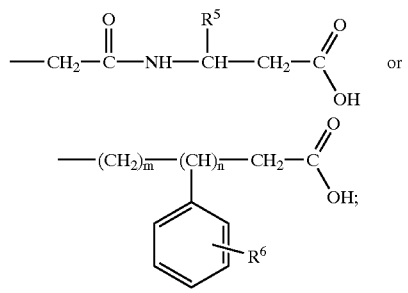

R² is

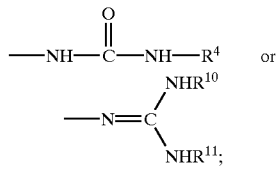

R³ is hydrogen, alkyl, cycloalkyl, aralkyl, aryl or carboxyalkyl;
R⁴ is alkyl or aralkyl;
R⁵ is hydrogen, alkyl, aryl, heterocyclyl or —CO—NH—R⁸;
R⁶ is hydrogen or

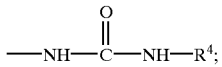

R⁷ is hydrogen, alkyl, cycloalkyl or aralkyl;
R⁸ is alkyl, cycloalkyl, aralkyl or aryl;
R⁹ is hydrogen, alkyl, cycloalkyl, aryl or aralkyl;
R¹⁰ and R¹¹ are each independently hydrogen or alkyl or R¹⁰ and R¹¹ together with the N-atoms to which they are attached form a 5- to 6-membered heterocyclic ring which can be alkyl-substituted;
X is —CH(R³)—;
Z is —N(R⁷)— or oxygen, wherein Y is —CO— when Z is —N(R⁷)— and Y is —CH(R⁹)— when Z is oxygen;
m, n and p are zero or whole positive numbers, wherein m is 2 to 5; n is zero or 1; p is zero or 1;
and their pharmaceutically usable salts and esters.

The compounds of formula I and their pharmaceutically usable salts and esters are novel and have valuable pharmacological properties. In particular, they inhibit the binding of adhesive proteins such as fibrinogen, vitronectin, von Willebrand factor, fibronectin, thrombospontin and osteopontin to the vitronectin receptors (such as e.g. $\alpha_v\beta_3$, $\alpha_v\beta_5$, $\alpha_v\beta_6$, $\alpha_v\beta_8$, etc.) on the surface of various types of cell. All of the compounds of formula I that were tested inhibited the binding of fibrinogen to the vitronectin receptor $\alpha_v\beta_3$ in the assay described below. Therefore these compounds can be used as vitronectin receptor agonists in the treatment and prophylaxis of illnesses which are caused by a malfunction of the binding of adhesive proteins to vitronectin receptors. In particular, they can be used as vitronectin receptor antagonists in the prophylaxis or treatment of neoplasms, tumor metastasis, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi.

Objects of the present invention are the compounds of formula I and their aforementioned salts and esters per se and their use as therapeutically active substances, a process for the manufacture of the said compounds, intermediates, pharmaceutical compositions, medicaments containing the said compounds, their salts or esters, the use of the said compounds, solvates and salts for the prophylaxis and/or therapy of illnesses, especially in the treatment or prophylaxis of, for example, neoplasms, tumor metasis, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi, and the use of the said compounds and salts for the production of medicaments for the treatment or prophylaxis of, for example, neoplasms, tumor metasis, tumor growth, osteoporosis, Paget's disease, diabetic retinopathy, restenosis following vascular intervention, psoriasis, arthritis, fibrosis, kidney failure as well as infections caused by viruses, bacteria or fungi.

DETAILED DESCRIPTION OF THE INVENTION

In the present description the term "alkyl", alone or in combination, signifies a straight-chain or branched-chain alkyl group with 1 to 8 carbon atoms, preferably a straight or branched-chain alkyl group with 1–4 carbon atoms. Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl, ethyl, propyl, isopropyl, butyl, 2-butyl, tert.butyl and pentyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl and particularly cyclopentyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, preferably methoxy and ethoxy.

The term "aryl", alone or in combination, signifies a phenyl or naphthyl group which optionally carries one or more substituents each independently selected from alkyl, alkoxy, halogen, carboxy, alkoxycarbonyl, aminocarbonyl, hydroxy, amino, nitro and the like, such as phenyl, p-tolyl, 4-methoxyphenyl, 4-tert.butoxyphenyl, 4-fluorophenyl, 2-chlorophenyl, 3-chlorophenyl, 4-chlorophenyl, 4-hydroxyphenyl, 1-naphthyl and 2-naphthyl. Preferred are carboxyphenyl, hydroxyphenyl and fluoro-phenyl and particularly phenyl.

The term "aralkyl", alone or in combination, signifies an alkyl or cycloalkyl group as previously defined in which one hydrogen atom has been replaced by an aryl group as previously defined. Preferred are benzyl, benzyl substituated with hydroxy or halogen, preferably fluorine. Particularly preferred is benzyl.

The term "heterocyclyl", alone or in combination, signifies a saturated, partially unsaturated or aromatic 5- to 10-membered heterocycle which contains one or more hetero atoms selected from nitrogen, oxygen and sulphur. If desired, it can be substituted on one or more carbon atoms by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e.=N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl. Preferred are 5- or 6-membered rings, especially pyridyl. Particularly preferred is 3-pyridyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc., preferably amino, dimethylamino and diethylamino and particularly primary amino.

The term "halogen" signifies fluorine, chlorine, bromine or iodine and preferably chlorine or bromine and particularly chlorine.

The term "carboxy", alone or in combination, signifies a —COOH group.

The term "carboxyalkyl" alone or in combination, signifies an alkyl group as previously described in which one hydrogen atom has been replaced by a carboxy group. The carboxymethyl group is preferred and particularly carboxyethyl.

The term "amino protecting group", alone or in combination, signifies any conventional amino protecting group. Examples of amino protecting groups include BOC and Cbz.

Examples of physiologically usable salts of the compounds of formula I are salts with physiologically compatible mineral acids such hydrochloric acid, sulphuric acid or phosphoric acid; or with organic acids such as methanesulphonic acid, acetic acid, trifluoroacetic acid, citric acid, fumaric acid, maleic acid, tartaric acid, succinic acid or salicylic acid. The compounds of formula I with free carboxy groups can also form salts with physiologically compatible bases. Examples of such salts are alkali metal, alkali earth metal, ammonium and alkylammonium salts such as the Na, K, Ca or tertramethylammonium salt. The compound of formula I can also be present in the form of zwitterions.

The invention expressly includes pharmaceutically suitable derivatives of the compounds of formula I. For example, the COOH groups in $R^1$ and $R^3$ can be esterified. The alkyl and aralkyl esters are examples of suitable esters. The methyl, ethyl, propyl, butyl, benzyl and (R/S)-1-((isopropoxy-carbonyl)-oxy)-ethyl esters are preferred esters. The methyl, ethyl and tert.butyl esters are especially preferred.

The compounds of formula I can also be solvated, e.g. hydrated. The solvation can be effected in the course of the manufacturing process or can take place e.g. as a consequence of hygroscopic properties of an initially anhydrous compound of formula I (hydration).

The compounds of formula I can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

In a preferred embodiment of the present invention $R^1$ is

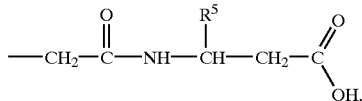

In a further preferred embodiment $R^1$ is

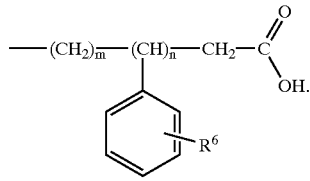

Also preferred are compounds according to formula I, wherein $R^2$ is

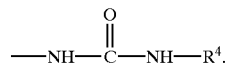

Further preferred are compounds according to formula I, wherein $R^2$ is

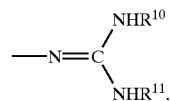

Another preferred embodiment of the invention comprises compounds of formula I, wherein $R^3$ is hydrogen, alkyl, aralkyl or carboxyalkyl, preferrably hydrogen, propyl, butyl, carboxyethyl, benzyl or benzyl substitued with hydroxy. Particularly preferred examples for $R^3$ are hydrogen, 2-propyl, 2-butyl, 2-carboxyethyl, benzyl and p-hydroxy-benzyl.

Further preferred compounds of the present invention are those, wherein $R^4$ is butyl, benzyl or benzyl substituted with halogen, particularly with fluorine. Particularly preferred examples for $R^4$ are n-butyl, benzyl and p-fluoro-benzyl.

Also preferred are the compounds according to formula I, wherein $R^5$ is hydrogen, methyl, phenyl, pyridyl or —CO—NH—$R^8$.

Another preferred aspect of the present invention are compounds according to formula I, wherein $R^6$ is hydrogen or —NH—CO—NH-benzyl.

Also preferred are compounds according to formula I, wherein $R^7$ is hydrogen or alkyl, particularly preferred hydrogen or methyl.

Another preferred embodiment of the present invention are compounds of formula I, wherein $R^8$ is aryl, preferably phenyl or substituted phenyl. Particularly preferred is phenyl substituted with carboxy.

Likewise preferred are compounds according to formula I, wherein $R^9$ is hydrogen or aryl. Particularly preferred is hydrogen and phenyl.

Also preferred are compounds of formula I in which $R^{10}$ and $R^{11}$ together with the N-atoms to which they are attached form an imidazolidine or a hexahydropyrimidine ring. Particularly preferred are the compounds according to formula 1, wherein $R^{10}$ and $R^{11}$ are hydrogen.

Another preferred object of the present invention comprises compounds of formula I, wherein p is 1 when Z is oxygen.

Other preferred compounds of formula I are those, wherein m is 2 to 4, preferably m is 3 to 4.

Further preferred compounds according to formula I are those, wherein n is 1.

Also preferred compounds of formula I are those in which p is 1.

Further preferred are compounds of formula I, wherein Z is —N($R^7$)—.

Another preferred embodiment of the present invention are compounds of formula I, wherein Z is oxygen.

In one embodiment of the derivative of formula I the compound has the formula

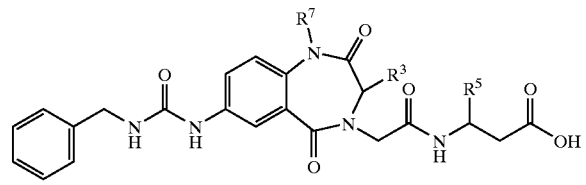

wherein $R^3$ is hydrogen, alkyl, unsubstituted benzyl, hydroxy-substituted benzyl, or carboxyalkyl; $R^5$ is hydrogen, alkyl having from 1 to 4 carbon atoms, or unsubstituted phenyl; and $R^7$ is hydrogen or alkyl having from 1 to 4 carbon atoms. In a more specific embodiment $R^3$ is hydrogen or alkyl. Examples of such compounds include (R,S)-3-[2-[7-(3-benzyl-ureido)-1-methyl-2,5-dioxo-1,2,3,5-tetrahydro-benzo[e][1,4]diazepin-4-yl]-acetylamino]-3-phenyl-propionic acid; 3-[2-[7-(3-benzyl-ureido)-1-methyl-2,5-dioxo-1,2,3,5-tetrahydro-benzo[e][1,4]diazepin-4-yl]-acetylamino]-propionic acid; 3-(R,S)-{2-[7-(3-benzyl-ureido)-(3-(S,S)-sec-butyl-2,5-dioxo-1,2,3,5-tetrahydro-benzo[e][1,4]diazepin-4-yl]-acetylamino}-3-phenyl-propionic acid; and 3-(R,S)-{2-[7-(3-benzyl-ureido)-3-(S)-isopropyl-2,5-dioxo-1,2,3,5-tetrahydro-benzo[e][1,4]diazepin-4-yl]-acetylamino}-butyric acid. In another more specific embodiment $R^3$ is unsubstituted benzyl, hydroxy-substituted benzyl or carboxyalkyl. Examples of such compounds include 3-(R,S)-{2-[7-(3-benzyl-ureido)-3-(S)-(4-hydroxy-benzyl)-2,5-dioxo-1,2,3,5-tetrahydro-benzo[e][1,4]diazepin-4-yl]-acetylamino}-3-phenyl-propionic acid; 3-(R,S)-{2-[7-(3-benzyl-ureido)-3-(S)-benzyl-2,5-dioxo-1,2,3,5-tetrahydro-benzo[e][1,4]diazepin-4-yl]-acetylamino}-3-phenyl-propionic acid; 3-(R,S)-{2-[7-(3-benzyl-ureido)-3-(S)-(2-carboxy-ethyl)-2,5-dioxo-1,2,3,5-tetrahydro-benzo[e][1,4]diazepin-4-yl]-acetylamino}-3-phenyl-propionic acid; 3-(R,S)-{2-[3-(S)-benzyl-7-(3-benzyl-ureido)-2,5-dioxo-1,2,3,5-tetrahydro-benzo[e][1,4]diazepin-4-yl]-acetylamino}-butyric acid; and 3-(R,S)-{2-[7-(3-benzyl-ureido)-3-(S)-(4-hydroxy-benzyl)-2,5-dioxo-1,2,3,5-tetrahydro-benzo [e][1,4]diazepin-4-yl]-acetylamino}-butyric acid.

In another embodiment of the derivative of formula I the compound has the formula

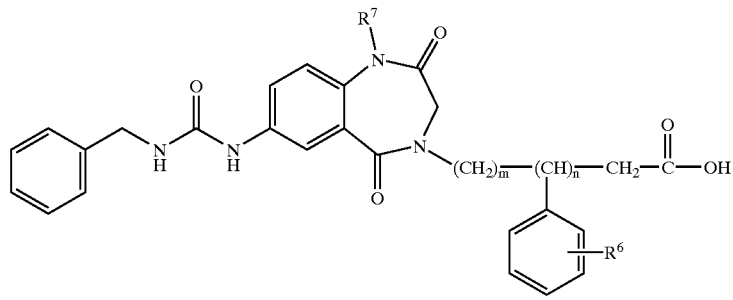

wherein m is from 2 to 5; n is zero or 1; $R^6$ is hydrogen or

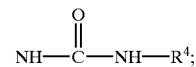

$R^4$ is aralkyl; and $R^7$ is hydrogen or alkyl having from 1 to 4 carbon atoms. Examples of such compounds include (R,S)-6-[7-(3-benzyl-ureido)-1-methyl-2,5-dioxo-1,2,3,5-tetrahydro-benzo[e][1,4]diazepin-4-yl]-3-[4-(3-benzyl-ureido)-phenyl]-hexanoic acid; 6-[7-(3-benzyl-ureido)-2,5-dioxo-1,2,3,5-tetrahydro-benzo[e][1,4]diazepin-4-yl]-hexanoic acid; and (R,S)-6-[7-(3-benzyl-ureido)-2,5-dioxo-1,2,3,5-tetrahydro-benzo[e][1,4]diazepin-4-yl]-3-phenyl-hexanoic acid.

In another embodiment of the derivative of formula I the compound has the formula

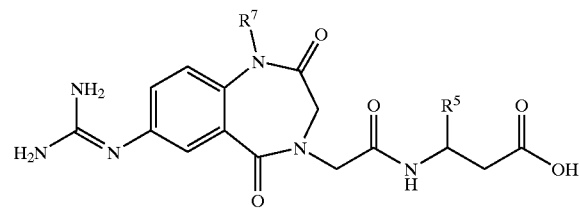

wherein R⁵ is hydrogen or unsubstituted phenyl; and R⁷ is hydrogen or alkyl having from 1 to 4 carbon atoms. Examples of such compounds include 3-[2-[7-(3-benzyl-ureido)-1-methyl-2,5-dioxo-1,2,3,5-tetrahydro-benzo[e][1,4]diazepin-4-yl]-acetylamino]-propionic acid; and 3-[2-(7-guanidino-1-methyl-2,5-dioxo-1,2,3,5-tetrahydro-benzo[e][1,4]diazepin-4-yl)-acetylamino]-propionic acid.

In another embodiment of the derivative of formula I the compound has the formula

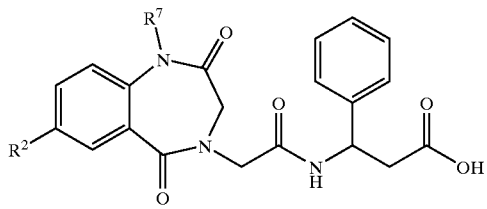

wherein R² is

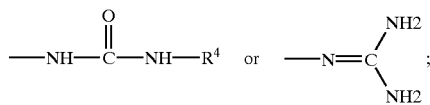

R⁴ is unsubstituted benzyl; and R⁷ is alkyl having from 1 to 4 carbon atoms. Examples of such compounds include (R,S)-3-[2-[6-(3-benzyl-ureido)-1-methyl-2,4-dioxo-1,4-dihydro-2H-quinazolin-3-yl]-acetylamino]-3-phenyl-propionic acid; and (R,S)-3-[2-(6-guanidino-1-methyl-2,4-dioxo-1,4-dihydro-2H-quinazolin-3-yl)-acetylamino]-3-phenyl-propionic acid.

In another embodiment of the derivative of formula I the compound has the formula

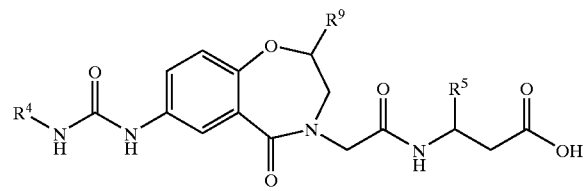

wherein
R⁴ is alkyl, unsubstituted benzyl or halo-substituted benzyl;
R⁵ is hydrogen, unsubstituted phenyl, pyridyl or

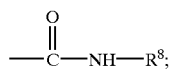

R⁸ is carboxy-substituted phenyl; and R⁹ is hydrogen or unsubstituted phenyl. In a more specific embodiment R⁵ is hydrogen and R⁹ is hydrogen. Examples of such compounds include 3-{2-[7-(3-benzyl-ureido)-5-oxo-2,3-dihydro-5H-benzo[f][1,4]oxazepin-4-yl]-acetylamino}-propionic acid. In another more specific embodiment R⁵ is unsubstituted phenyl. Examples of such compounds include (R,S)-3-[2-[7-(3-benzyl-ureido)-5-oxo-2,3-dihydro-5H-benzo[f][1,4]oxazepin-4-yl]-acetylamino]-3-phenyl-propionic acid; and (R,S)-3-{2-[7-(3-benzyl-ureido)-5-oxo-2-phenyl-2,3-dihydro-5H-benzo[f][1,4]oxazepin-4yl]-acetylamino}-3-phenyl-propionic acid. In another more specific embodiment R⁵ is 3-pyridyl. Examples of such compounds include (R,S)-3-{2-[7-(3-benzyl-3-methyl-ureido)-5-oxo-2,3-dihydro-5H-benzo[f][1,4]oxazepin-4-yl]-acetylamino}-3-pyridin-3-yl-propionic acid hydrochloride; (R,S)-3-{2-[7-(3-butyl-ureido)-5-oxo-2,3-dihydro-5H-benzo[f][1,4]oxazepin-4-yl]-acetylamino}-3-pyridin-3-yl-propionic acid; and (R,S)-3-(2-{7-[3-(4-fluoro-benzyl)-ureido]-5-oxo-2,3-dihydro-5H-benzo[f][1,4]oxazepin-4-yl}-acetylamino)-3-pyridin-3-yl-propionic acid. In another more specific embodiment R⁵ is —C(O)NHR⁸ and R⁸ is carboxy-substituted phenyl. Examples of such compounds include (S)-2-[2-[2-[7-(3-benzyl-ureido)-5-oxo-2,3-dihydro-5H-benzo[f][1,4]oxazepin-4-yl]-acetylamino]-3-carboxy-propionylamino]-benzoic acid.

Examples of preferred compounds of formula I are:

(R,S)-3-[2-[7-(3-benzyl-ureido)-1-methyl-2,5-dioxo-1,2,3,5-tetrahydro-benzo[e][1,4]diazepin-4-yl]-acetylamino]-3-phenyl-propionic acid;
(R,S)-3-[2-(7-guanidino-1-methyl-2,5-dioxo-1,2,3,5-tetrahydro-benzo[e][1,4]diazepin-4-yl)-acetylamino]-3-phenyl-propionic acid hydrochloride;
3-[2-[7-(3-benzyl-ureido)-1-methyl-2,5-dioxo-1,2,3,5-tetrahydro-benzo[e][1,4]diazepin-4-yl]-acetylamino]-propionic acid;
3-[2-(7-guanidino-1-methyl-2,5-dioxo-1,2,3,5-tetrahydro-benzo[e][1,4]diazepin-4-yl)-acetylamino]-propionic acid hydrochloride;
(R,S)-6-[7-(3-benzyl-ureido)-1-methyl-2,5-dioxo-1,2,3,5-tetrahydro-benzo[e][1,4]diazepin-4-yl]-3-[4-(3-benzyl-ureido)-phenyl]-hexanoic acid;
3-(R,S)-{2-[7-(3-benzyl-ureido)-3-(S)-(4-hydroxy-benzyl)-2,5-dioxo-1,2,3,5-tetrahydro-benzo[e][1,4]diazepin-4-yl]-acetylamino}-3-phenyl-propionic acid;
3-(R;S)-{2-[7-(3-benzyl-ureido)-3-(S)-benzyl-2,5-dioxo-1,2,3,5-tetrahydro-benzo[e][1,4]diazepin-4-yl]-acetylamino}-3-phenyl-propionic acid;
3-(R,S)-{2-[7-(3-benzyl-ureido)-3-(S,S)-sec-butyl-2,5-dioxo-1,2,3,5-tetrahydro-benzo[e][1,4]diazepin-4-yl]-acetylamino}-3-phenyl-propionic acid;
3-(R,S)-{2-[7-(3-benzyl-ureido)-3-(S)-(2-carboxy-ethyl)-2,5-dioxo-1,2,3,5-tetrahydro-benzo[e][1,4]diazepin-4-yl]-acetylamino}-3-phenyl-propionic acid
3-(R,S)-{2-[3-(S)-benzyl-7-(3-benzyl-ureido)-2,5-dioxo-1,2,3,5-tetrahydro-benzo[e][1,4]diazepin-4-yl]-acetylamino}-butyric acid;
3-(R,S)-{2-[7-(3-benzyl-ureido)-3-(S)-(4-hydroxy-benzyl)-2,5-dioxo-1,2,3,5-tetrahydro-benzo[e][1,4]diazepin-4-yl]-acetylamino}-butyric acid;
3-(R,S)-{2-[7-(3-benzyl-ureido)-3-(S)-isopropyl-2,5-dioxo-1,2,3,5-tetrahydro-benzo[e][1,4]diazepin-4-yl]-acetylamino}-butyric acid;
(R,S)-3-[2-[6-(3-benzyl-ureido)-1-methyl-2,4-dioxo-1,4-dihydro-2H-quinazolin-3-yl]-acetylamino]-3-phenyl-propionic acid);
(R,S)-3-[2-(6-guanidino-1-methyl-2,4-dioxo-1,4-dihydro-2H-quinazolin-3-yl)-acetylamino]-3-phenyl-propionic acid;
3-{2-[7-(3-benzyl-ureido)-5-oxo-2,3-dihydro-5H-benzo[f][1,4]oxazepin-4-yl]-acetylamino}-propionic acid;
(R,S)-3-[2-[7-(3-benzyl-ureido)-5-oxo-2,3-dihydro-5H-benzo[f][1,4]oxazepin-4-yl]-acetylamino]-3-phenyl-propionic acid;
(R,S)-3-{2-[7-(3-benzyl-3-methyl-ureido)-5-oxo-2,3-dihydro-5H-benzo[f][1,4]oxazepin-4-yl]-acetylamino}-3-pyridin-3-yl-propionic acid hydrochloride;
(S)-2-[2-[2-[7-(3-benzyl-ureido)-5-oxo-2,3-dihydro-5H-benzo[f][1,4]oxazepin-4-yl]-acetylamino]-3-carboxy-propionylamino]-benzoic acid as acetate salt;

(R,S)-3-{2-[7-(3-butyl-ureido)-5-oxo-2,3-dihydro-5H-benzo[f][1,4]oxazepin-4-yl]-acetylamino}-3-pyridin-3-yl-propionic acid;
(R,S)-3-(2-{7-[3-(4-fluoro-benzyl)-ureido]-5-oxo-2,3-dihydro-5H-benzo[f][1,4]oxazepin-4-yl}-acetylamino)-3-pyridin-3-yl-propionic acid;
(R,S)-3-{2-[7-(3-benzyl-ureido)-5-oxo-2-phenyl-2,3-dihydro-5H-benzo[f][1,4]oxazepin-4-yl]-acetylamino}-3-phenyl-propionic acid;
6-[7-(3-benzyl-ureido)-2,5-dioxo-1,2,3,5-tetrahydro-benzo[e][1,4]diazepin-4yl]-hexanoic acid;
(R,S)-6-[7-(3-benzyl-ureido)-2,5-dioxo-1,2,3,5-tetrahydro-benzo[e][1,4]diazepin-4-yl]-3-phenyl-hexanoic acid.

Examples of particularly preferred compounds of formula I are
(R,S)-3-[2-[7-(3-benzyl-ureido)-1-methyl-2,5-dioxo-1,2,3,5-tetrahydro-benzo[e][1,4]diazepin-4-yl]-acetylamino]-3-phenyl-propionic acid;
3-[2-[7-(3-benzyl-ureido)-1-methyl-2,5-dioxo-1,2,3,5-tetrahydro-benzo[e][1,4]diazepin-4-yl]-acetylamino]-propionic acid;
(R,S)-6-[7-(3-benzyl-ureido)-1-methyl-2,5-dioxo-1,2,3,5-tetrahydro-benzo[e][1,4]diazepin-4-yl]-3-[4-(3-benzyl-ureido)-phenyl]-hexanoic acid;
3-(R,S)-{2-[7-(3-benzyl-ureido)-3-(S)-(4-hydroxy-benzyl)-2,5-dioxo-1,2,3,5-tetrahydro-benzo[e][1,4]diazepin-4-yl]-acetylamino}-3-phenyl-propionic acid;
3-(R,S)-{2-[7-(3-benzyl-ureido)-3-(S)-(4-hydroxy-benzyl)-2,5-dioxo-1,2,3,5-tetrahydro-benzo[e][1,4]diazepin-4-yl]-acetylamino}-butyric acid;
(R,S)-3-[2-[7-(3-benzyl-ureido)-5-oxo-2,3-dihydro-5H-benzo[f][1,4]oxazepin-4-yl]-acetylamino]-3-phenyl-propionic acid;
(R,S)-3-{2-[7-(3-benzyl-3-methyl-ureido)-5-oxo-2,3-dihydro-5H-benzo[f][1,4]oxazepin-4-yl]-acetylamino}-3-pyridin-3-yl-propionic acid hydrochloride;
(R,S)-3-{2-[7-(3-butyl-ureido)-5-oxo-2,3-dihydro-5H-benzo[f][1,4]oxazepin-4-yl]-acetylamino}-3-pyridin-3-yl-propionic acid;
(R,S)-3-(2-{7-[3-(4-fluoro-benzyl)-ureido]-5-oxo-2,3-dihydro-5H-benzo[f][1,4]oxazepin-4-yl}-acetylamino)-3-pyridin-3-yl-propionic acid;
(R,S)-3-{2-[7-(3-benzyl-ureido)-5-oxo-2-phenyl-2,3-dihydro-5H-benzo[f][1,4]oxazepin-4-yl]-acetylamino}-3-phenyl-propionic acid;
(R,S)-6-[7-(3-benzyl-ureido)-2,5-dioxo-1,2,3,5-tetrahydro-benzo[e][1,4]diazepin-4-yl]-3-phenyl-hexanoic acid.

Processes for the manufacture of compounds of formula I are an object of the invention.

The substituents and indices used in the following Schemes have the significances given above unless indicated to the contrary.

Compounds of formula II

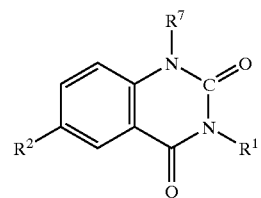

can be prepared according to the Schemes 1 to 4.

The corresponding quinazoline-2,4-diones might be prepared as shown in Scheme 1.

Scheme 1

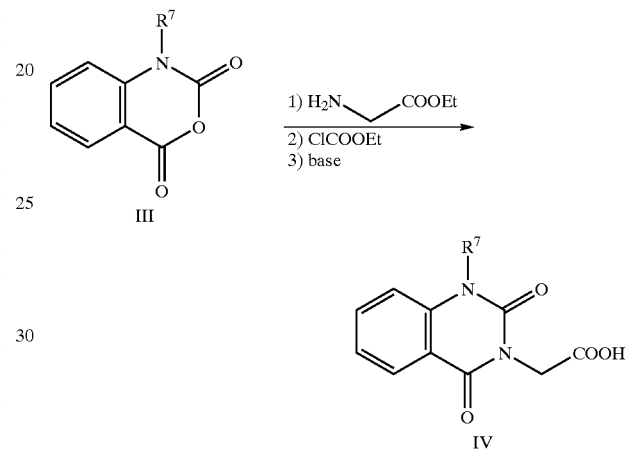

Reaction of a substituted 3,1-benzoxazine-2,4-dione III with glycine ethyl ester followed by treatment with ethylchloroformate and then with base (e.g. KOH aq.) gave the acid IV (M.Süsse and S. Johne, Monatshefte. Chemie, 1987, 118, 71–79). Compounds of formula III, wherein $R^7$ is alkyl, cycloalkyl or aralkyl can be obtained by reacting a compound according to formula III, wherein $R^7$ is hydrogen with the corresponding alkyl halide, cycloalkyl halide or aralkyl halide in the presence of NaH in THF or dioxan. The corresponding compound III, wherein $R^7$ is hydrogen is known in the art.

Nitration of IV followed by coupling with a 3-substituted beta-alanine ester and catalytic hydrogenation led to the formation of V (Scheme 2).

Scheme 2

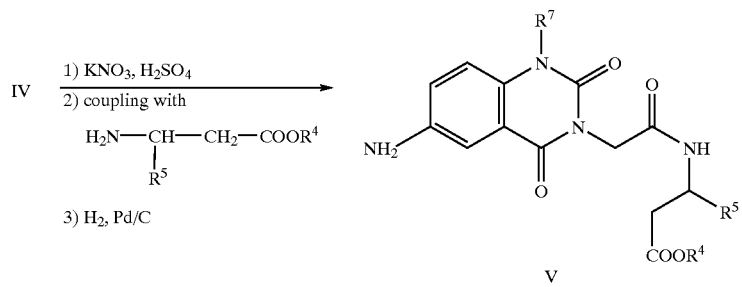

-continued

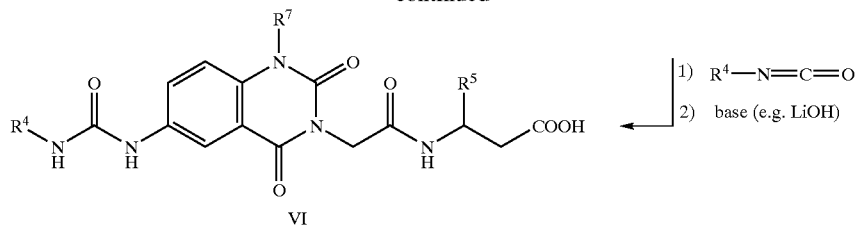

VI

Reaction of V with an isocyanate R⁴—N=C=O followed by ester hydrolysis produced the carboxylic acid VI.

By using an amine of type VII instead of glycine ethyl ester the intermediate VIII might be prepared (Scheme 3).

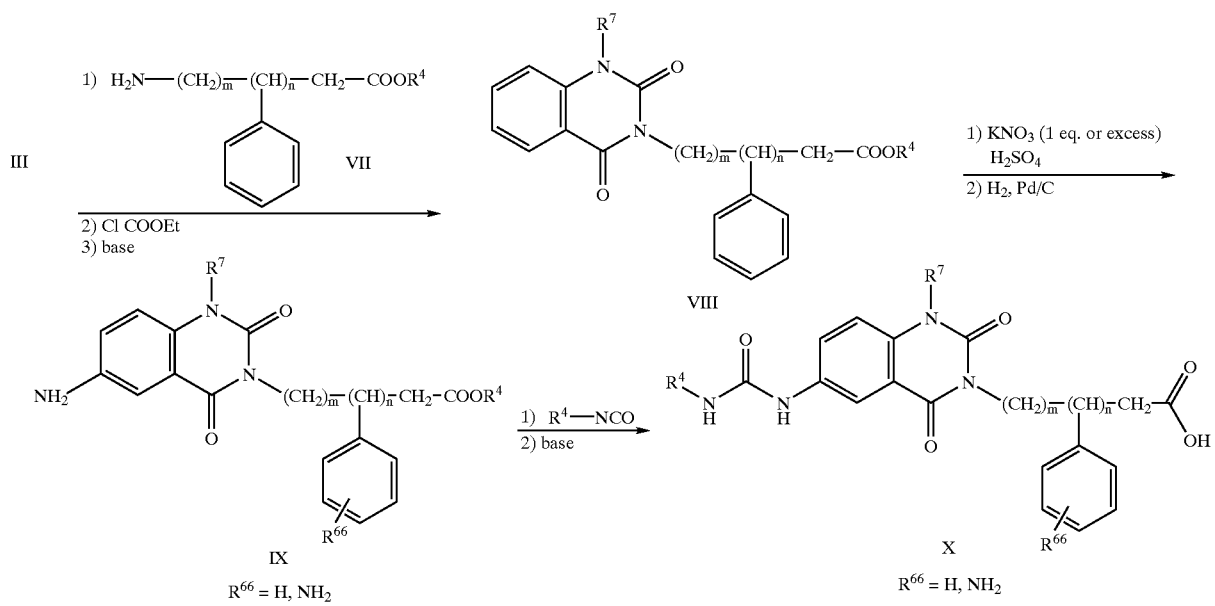

Scheme 3

Compounds according to formula X, wherein $R^{66}$ means

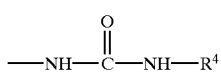

can be obtained by the reaction of compounds of formula X, wherein $R^{66}$ is $NH_2$ with an isocyanate $R^4$—N=C=O in the presence of a base.

A related sequence of reactions as shown in Scheme 2 was then applied to complete the synthesis of compounds of type X (via IX).

For the preparation of the guanidine derivatives XI the corresponding amines V (Scheme 2) or IX ($R^{66}$=H, NHCONHR⁴, Scheme 3) might be reacted with N,N'-bis(tert-butoxycarbonyl)-S-methylisothiourea (R. J. Bergeron and J. S. McManis, J. Org. Chem., 1987, 52, 1700–1703) in the presence of Hg(OAc)₂. Removal of the protective groups with TFA followed by ester hydrolysis gave the desired guanidino carboxylates XI (Scheme 4).

Scheme 4

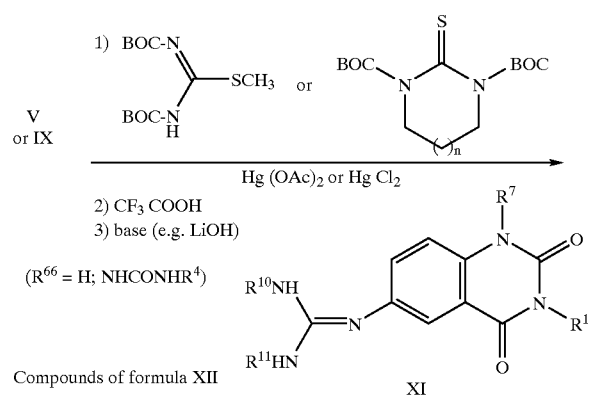

Compounds of formula XII

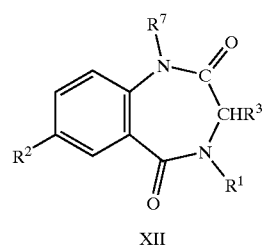

XII can be prepared according to the Schemes 5 to 8.

Scheme 5 illustrates the method used for the preparation of the benzodiazepinediones XVI and XVII. Briefly, in an "Ugi-type" four component reaction (see e.g. T. A. Keating and R. W. Armstrong, J. Org. Chem., 1996, 61, 8935–39) a 3-substituted 3-isocyano-propionic acid was reacted with 5-N-acetylamino-2-azidobenzoic acid (obtained by reaction of 5-N-acetylamino-2-aminobenzoic acid with sodium nitrite in the presence of HCl) and an adequately protected alpha amino acid derivative (e.g. t-butylester or benzylester) in the presence of formaldehyde to give the intermediate XIV. Upon treatment with polymer bound triphenylphosphine followed by heating and cleavage of the acetamide group the bicyclic amine XV was obtained. Completion of the synthesis of the corresponding urea (XVI) or guanidino (XVII) derivatives required methods already described in Schemes 2 and 3 or Scheme 4, respectively. The corresponding 3-substituted 3-isocyano-propionic acid can be obtained by formylating the corresponding amines in the presence of formic acid and silicon hydride (Jerry March, Wiley-Interscience, 4. edition, page 419). The isonitriles can also be prepared by elimination of water from the corresponding N-alkylformamides according to Ugi, Angew. Chem. Int. Ed. Engl. 4, 472–484 (1965).

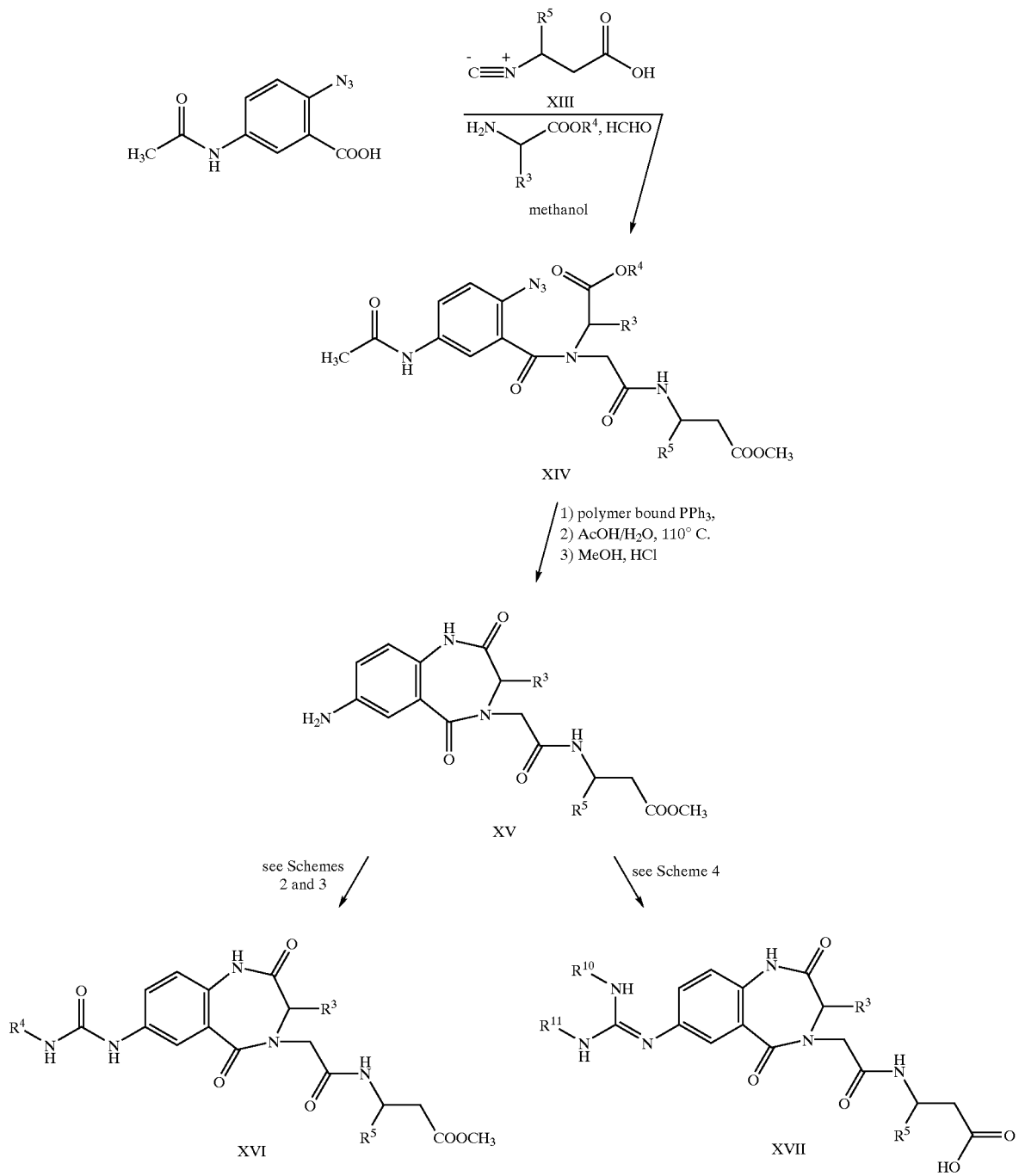

In a rather similar way, illustrated in Scheme 6, the benzodiazepinediones XXI and XXII could be prepared. In the event, an omega amino acid XVIII was reacted with 5-N-acetylamino-2-azidobenzoic acid (obtained by reaction of 5-N-acetylamino-2-aminobenzoic acid with sodium nitrite in the presence of HCl) in the presence of an aldehyde as well as an isonitrile to give XIX. The completion of the synthesis of XXI and XXII followed the same route as described in Scheme 5. The preparation of XVIII is described in EP 98100006. Briefly, triethylphosphonoacetate was reacted with (4-oxo-4-phenyl-butyl)carbamic acid t-butylester in the presence of sodium ethoxide. The resulting product was reduced by catalytic hydrogenation and the protective group cleaved upon treatment with HCl in EtOAc to give (R,S)-6-amino-3-phenyl-hexanoic acid ethyl ester which could be hydrolysed to the corresponding acid.

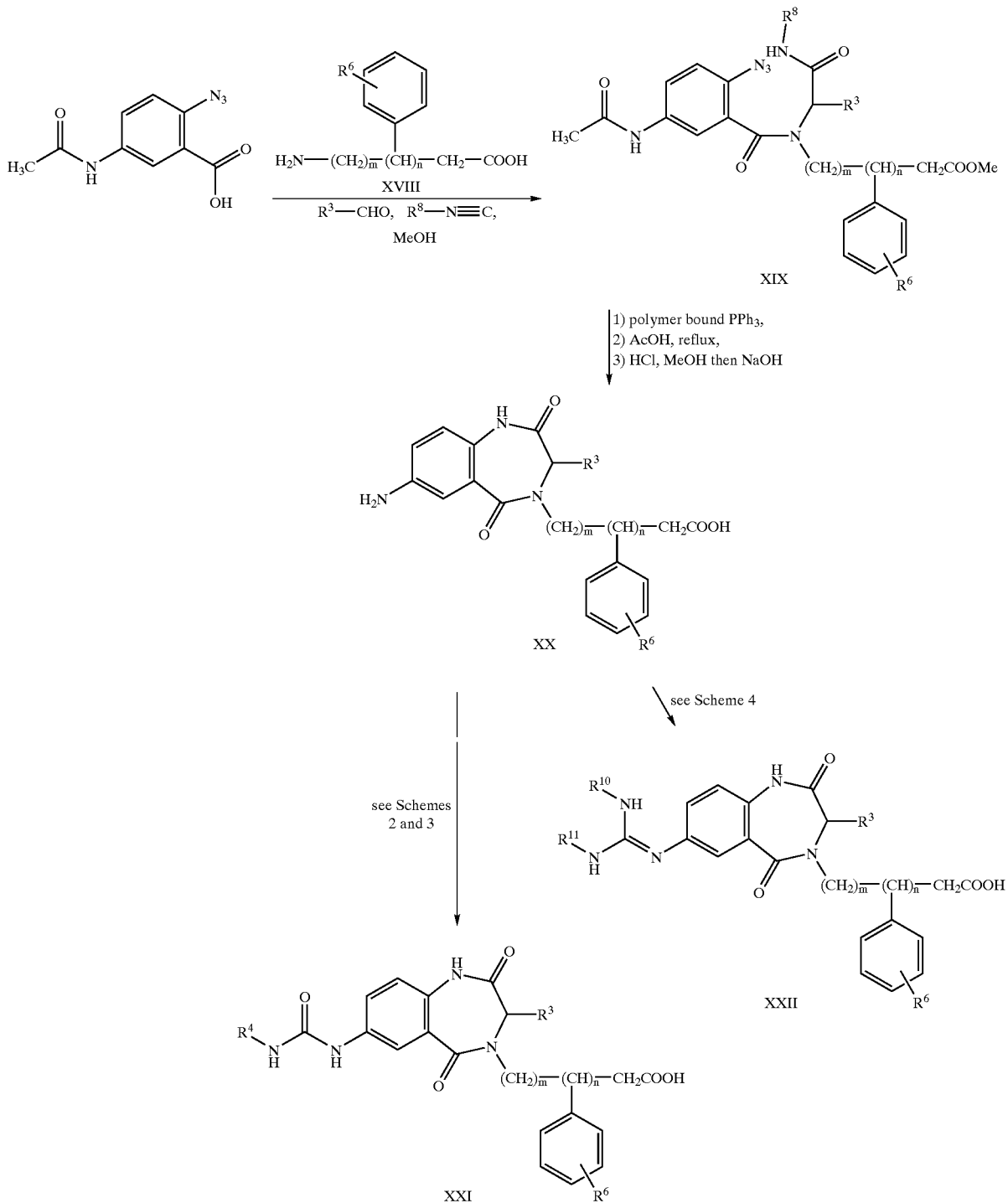

Scheme 6

In case R[7] is not hydrogen the routes illustrated in Scheme 7 and 8 might be used to prepare the desired benzodiazepinediones (for a similar strategy see e.g. B. K. Blackburn et al., J. Med. Chem. 1997, 40, 717–729). Specifically, a substituted isatoic acid anhydride (see e.g. G. M. Coppola, J. Heterocyclic Chem. 1986, 23, 233) was converted to the intermediates XXIII or XXIX by the three step sequence shown. Nitration followed by reduction of the nitro group yielded the amine XXIV (Scheme 7). The desired urea derivatives XXVII and the guanidino derivative XXVIII were then prepared via XXV and XXVI, respectively, using methods already discussed in Schemes 2, 3, and 4. A closely related strategy was applied to the completion of the synthesis of the derivatives XXX and XXXI (Scheme 8).

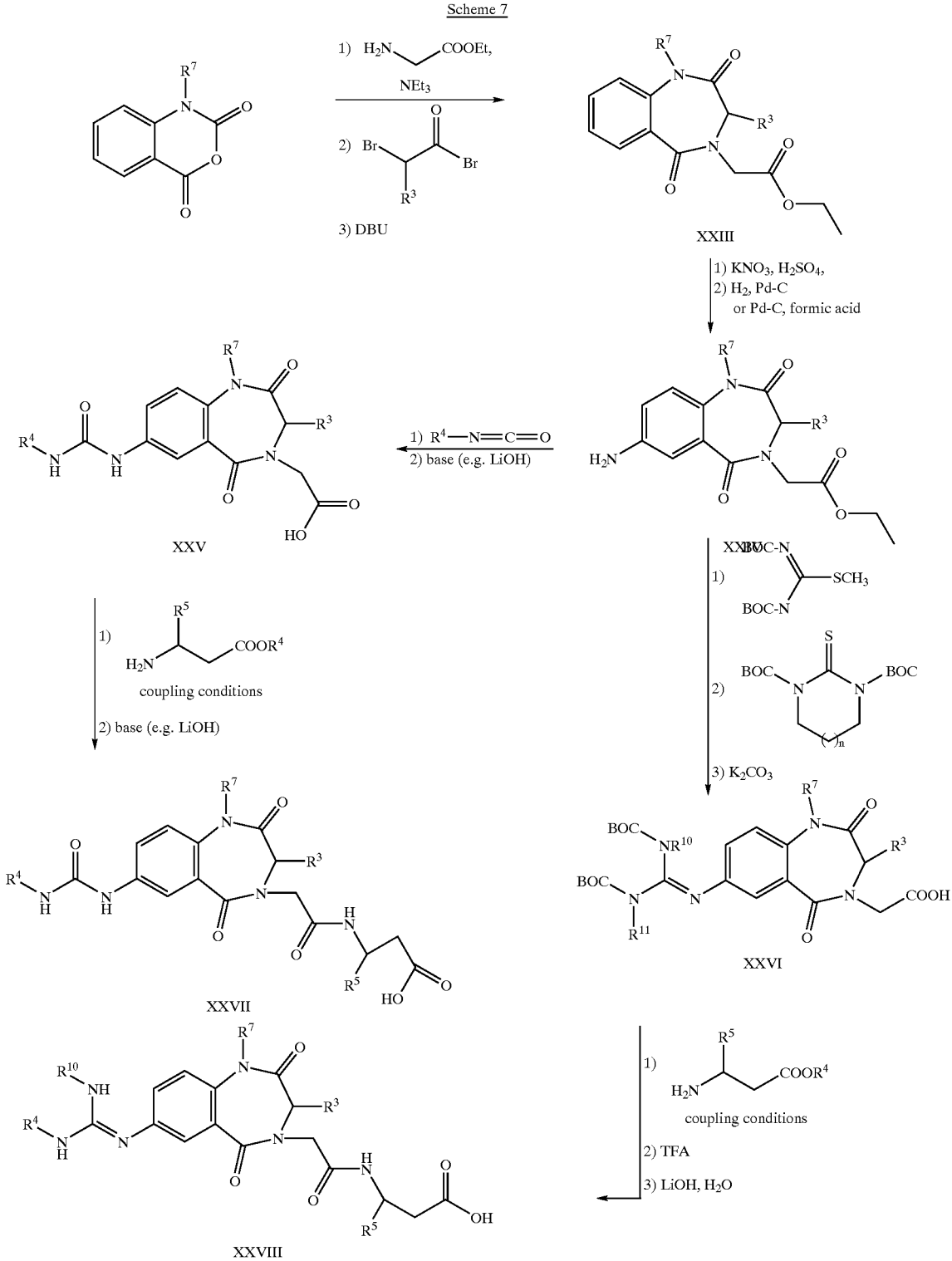

Scheme 8

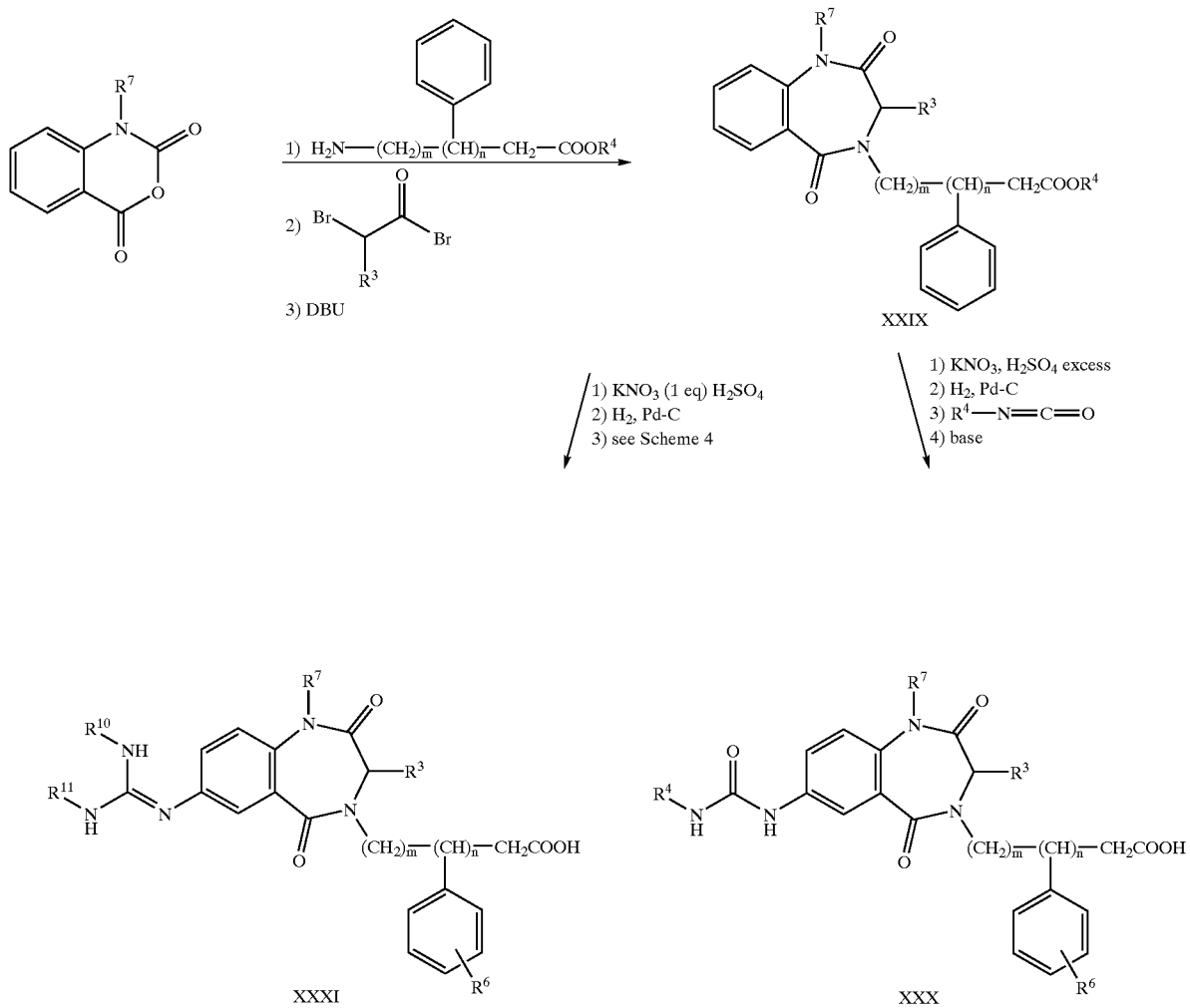

Compounds of formula XXXII

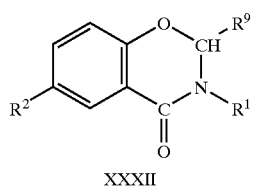

XXXII can be prepared according to Scheme 9.

The benzoxazoline derivatives XXXIV and XXXV might be prepared by the general methodology outlined in Scheme 9. Briefly, 5-N-Cbz-2-hydroxybenzoic acid or 5-nitro-2-hydroxybenzoic acid might be coupled with the corresponding omega amino acid ester derivatives using standard reaction conditions (e.g. in the presence of HBTU and NMM). Reaction of the benzamides obtained with an aldehyde $R^9$—CHO (see e.g. T. Miyake et al., Tetrahedron Letters 1996, 37, 3129 or J. M. Takacs et al., Tetrahedron Letters 1989, 30, 7321) followed by either removal of the protective group or reduction of the nitro group yielded the amino derivatives XXXIII. For the completion of the synthesis of the benzoxazoline derivatives XXXIV and XXXV the methods described in Schemes 2, 3, and 4 could be applied.

Scheme 9

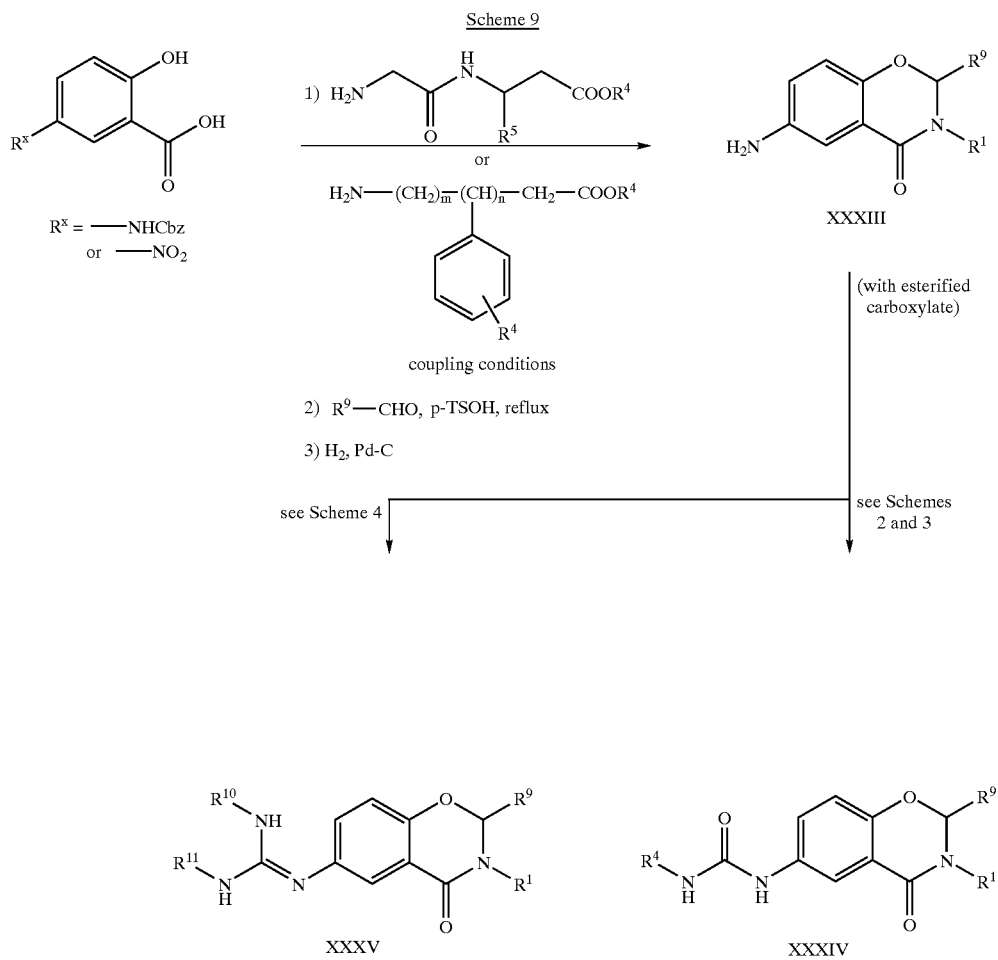

Compounds of formula XXXVI

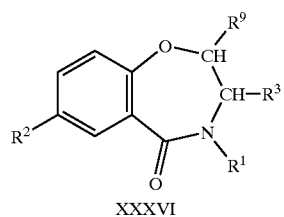

can be prepared according to Schemes 10 and 11.

Scheme 10 is illustrative of the methodology useful for preparing the benzoxazepine derivatives XXXX and XXXXI. Specifically, coupling of 2-fluoro-5-nitro-benzoic acid (Aldrich) with a substituted (2-hydroxy-ethylamino)-acetic acid derivative of type XXXVII (see e.g. G. Breipohl et al., Tetrahedron 1997, 53, 14671 and H. Kotsuki et al., Chem Lett 1994, 11, 2159), followed by cyclization and ester cleavage afforded the intermediate XXXVIII. Standard coupling of XXXVIII with a 3-substituted beta-alanine ester followed by reduction of the aromatic nitro group led to the formation of the chain elongated amine XXXIX. Completion of the synthesis of the corresponding guanidino (XXXX) or urea (XXXXI) derivatives required methods already described in Scheme 4 or Schemes 2 and 3, respectively.

Scheme 10

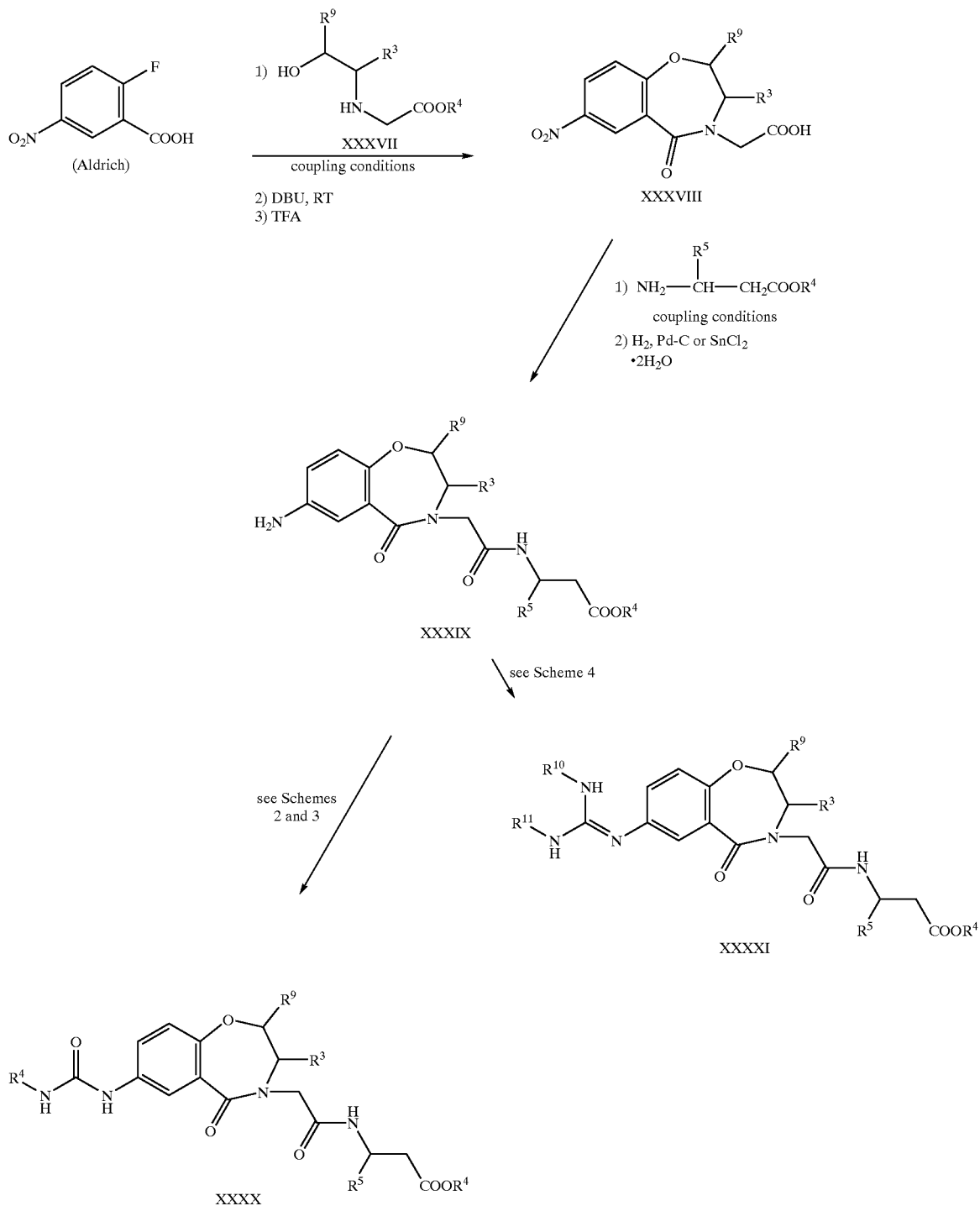

Instead of the glycine derivative XXXVII (Scheme 10) the amino esters XXXXIII could be employed (Scheme 11). These, in turn, might be prepared by reaction of XXXXII with i) a corresponding epoxide (see e.g. S. V. D'Andrea et al., J. Org. Chem. 1991, 56, 3133 or Q. Liu et al., Synlett 1995, 1037) or ii) an alpha bromo ketone followed by reduction with $NaBH_4$ (see e.g. M. Ohba et al., Chem. Pharm. Bull. 1992, 40, 2543) or iii) an alpha hydroxy ketone in the presence of $NaBH_4$ (see e.g. M. Peerzada, Org. Prep. Proceed. Int. 1985, 17, 267).

The completion of the synthesis of XXXXIV or XXXXV (Scheme 11) was achieved according to the methodology illustrated in Scheme 10.

Scheme 11
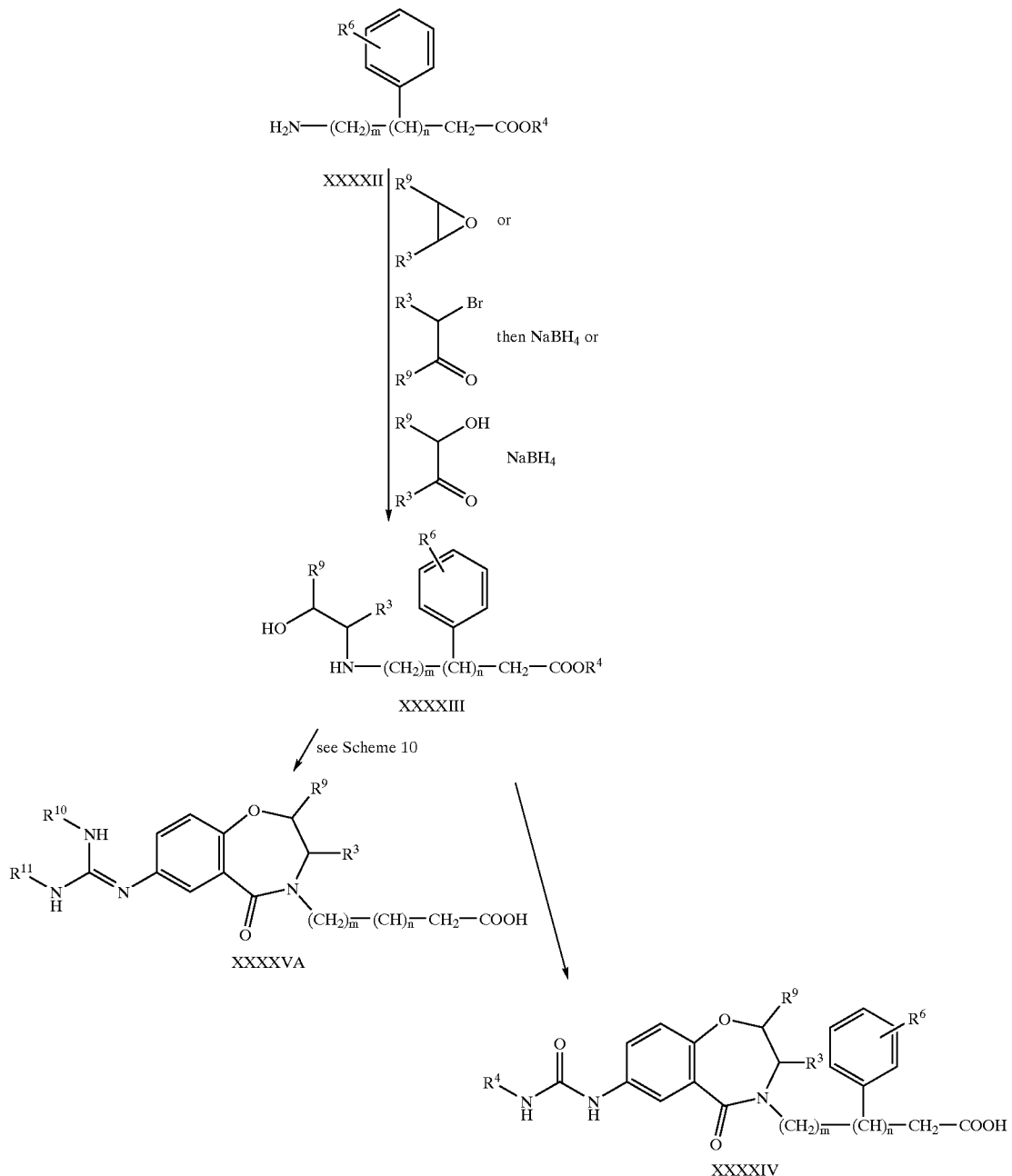
A preferred process for the preparation of a compound according to formula I, comprising one of the following steps:
5 a) reacting a compound of formula XXXXV
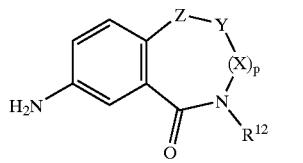
with an isocyanate of the formula $R^4$—N=C=O, wherein $R^{12}$ is
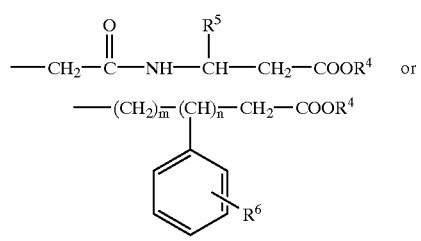

and $R^3$ to $R^{11}$, X, Y, Z, m,n and p are as defined above for formula I, and then treating the resulting compound to hydrolyze the resulting ester group contained in $R^{12}$; or b) reacting a compound of the formula XXXXV with guanylation agent (see for example Yaw Fui Yong et al., Tetrahedron Letters, 1999, 40, 53–56), preferably N,N'-bis(tert-butoxycarbonyl)-S-methylisothiourea in the presence of $Hg(OAc)_2$ or $HgCl_2$, wherein $R^3$ to $R^{12}$, X, Y, Z, m,n and p are defined as under a), and then treating the resulting compound to hydrolyze the resulting ester group contained in $R^{12}$; or c) reacting a compound of formula XXXXVI

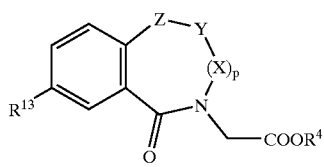

XXXXVI with $H_2N$—$CH(R^5)$—$CH_2$—$COOR^4$ under coupling conditions (e.g. HBTU in the presence of NMM), wherein $R^{13}$ is

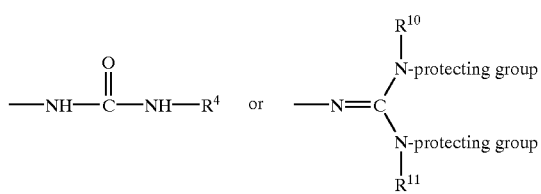

and $R^3$ to $R^{11}$, X, Y, Z, m,n and p are as defined above for formula I. The protecting group in $R^{13}$ is an amino protecting group such as for example Cbz (see e.g. R. J. Bergeron and J. S. Mc Manis, J. Org. Chem. 1987, 52, 1700–1703) and preferably BOC; treating the resulting compound to hydrolyze the ester group containing $R^4$ and yield the corresponding carboxylic acid, and when $R^{13}$ is the second group shown above, treating the resulting compound to remove the amino protecting groups. Removal of the amino protecting groups can be done before, at the same time, or after hydrolysis of the ester groups. The protecting group Cbz can be removed as described in Bergeron and McManis. BOC can be removed under acid conditions.

The invention also includes intermediates of formula XXXXV and XXXXVI

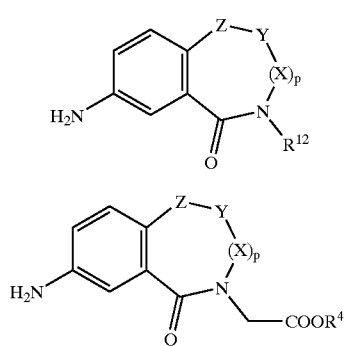

XXXXV

XXXXVI wherein $R^{12}$ is

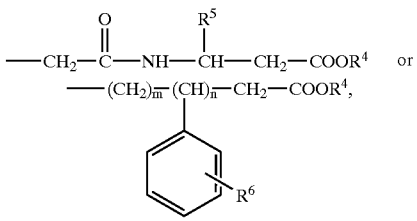

$R^{13}$ is

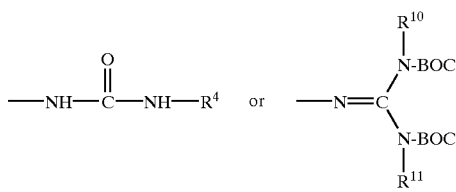

and $R^3$ to $R^{11}$, X, Y, Z, m,n and p are as defined above for compounds of formula I.

In an embodiment of the compound of formula XXXXV, X is —$CH(R^3)$—; $R^3$ is hydrogen, alkyl, aralkyl, or carboxyalkyl; $R^{12}$ is

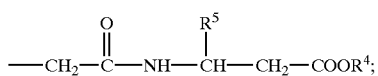

$R^4$ is alkyl; and $R^5$ is hydrogen, alkyl or aryl. Examples of such compounds include 3-[2-(7-amino-5-oxo-2,3-dihydro-5H-benzo[f][1,4]oxazepin-4-yl)-acetylamino]-propionic acid ethyl ester. In a more specific embodiment, in addition Z is —$N(R^7)$—; Y is —CO—; and $R^7$ is hydrogen or alkyl. Examples of compounds of such more specific embodiment include (R,S)-3-[2-(6-amino-1-methyl-2,4-dioxo-1,4-dihydro-2H-quinazolin-3-yl)-acetylamino]-3-phenyl-propionic acid ethyl ester. In still more specific embodiments $R^7$ is hydrogen; and p is 1. Examples of such compounds in which $R^3$ is alkyl include 3-(R,S)-[2-(7-amino-3-(S,S)-sec-butyl-2,5-dioxo-1,2,3,5-tetrahydro-benzo[e][1,4]diazepin-4-yl)-acetylamino]-3-phenyl-propionic acid methyl ester; and 3-(R,S)-[2-(7-amino-3-(S)-isopropyl-2,5-dioxo-1,2,3,5-tetrahydro-benzo[e][1,4]diazepin-4-yl)-acetylamino]-butyric acid methyl ester. Examples of such compounds in which $R^3$ is aralkyl include 3-(R,S)-{2-[7-amino-3-(S)-(4-hydroxy-benzyl)-2,5-dioxo-1,2,3,5-tetrahydro-benzo[e][1,4]diazepin-4-yl]-acetylamino}-3-phenyl-propionic acid methyl ester; 3-(R,S)-[2-(7-amino-3-(S)-benzyl-2,5-dioxo-1,2,3,5-tetrahydro-benzo[e][1,4]diazepin-4-yl)-acetylamino]-3-phenyl-propionic acid methyl ester; 3-(R,S)-{2-[7-Amino-3-(S)-benzyl-2,5-dioxo-1,2,3,5-tetrahydro-benzo[e][1,4]-diazepin-4-yl]-acetylamino}-butyric acid methyl ester; and 3-(R,S)-{2-[7-amino-3-(S)-(4-hydroxy-benzyl)-2,5-dioxo-1,2,3,5-tetrahydro-benzo[e][1,4]diazepin-4-yl]-acetylamino}-butyric acid methyl ester. Examples of such compounds in which $R^3$ is carboxyalkyl include 3-(R,S)-{2-[7-Amino-3-(S)-(2-methoxycarbonyl-ethyl)-2,5-dioxo-1,2,3,5-tetrahydro-benzo[e][1,4]diazepin-4-yl]-acetylamino}-3-phenyl-propionic acid methyl ester.

In an embodiment of the compound of formula XXXXVI, Z is —$N(R^7)$—; $R^7$ is alkyl; Y is —CO—; X is —$CH(R^3)$—; $R^3$ is hydrogen; p is 1; and $R^4$ is alkyl. Examples of such compounds include [7-(3-benzyl-ureido)-1-methyl-2,5-dioxo-1,2,3,5-tetrahydro-benzo[e][1,4]diazepin-4-yl]-acetic acid ethyl ester; and (7-N$^2$, N$^3$-bis(tert-butoxycarbonyl) guanidino-1-methyl-2,5-dioxo-1,2,3,5-tetrahydro-benzo[e] [1,4]diazepin-4-yl)-acetic acid ethyl ester.

Especially preferred intermediates are:

(1-methyl-7-nitro-2,5-dioxo-1,2,3,5-tetrahydro-benzo[e][1,4]diazepin-4-yl)-acetic acid ethyl ester;
(7-amino-1-methyl-2,5-dioxo-1,2,3,5-tetrahydro-benzo[e][1,4]diazepin-4-yl)-acetic acid ethyl ester;
[7-(3-benzyl-ureido)-1-methyl-2,5-dioxo-1,2,3,5-tetrahydro-benzo[e][1,4]diazepin-4-yl]-acetic acid ethyl ester;
[7-(3-benzyl-ureido)-1-methyl-2,5-dioxo-1,2,3,5-tetrahydro-benzo[e][1,4]diazepin-4-yl]-acetic acid;
(R,S)-3-[2-[7-(3-benzyl-ureido)-1-methyl-2,5-dioxo-1,2,3,5-tetrahydro-benzo[e][1,4]diazepin-4-yl]-acetylamino]-3-phenyl-propionic acid ethyl ester;
(7-N$^2$, N$^3$-bis(tert-butoxycarbonyl)guanidino-1-methyl-2,5-dioxo-1,2,3,5-tetrahydro-benzo[e][1,4]diazepin-4-yl)-acetic acid ethyl ester;
(7-N$^2$, N$^3$-bis(tert-butoxycarbonyl)guanidino-1-methyl-2,5-dioxo-1,2,3,5-tetrahydro-benzo[e][1,4]diazepin-4-yl)-acetic acid;
(R,S)-3-[2-(7-(N$^2$, N$^3$-bis(tert-butoxycarbonyl)guanidino-1-methyl-2,5-dioxo-1,2,3,5-tetrahydro-benzo[e][1,4]diazepin-4-yl)-acetylamino]-3-phenyl-propionic acid ethyl ester;
3-[2-(1-methyl-2,5-dioxo-1,2,3,5-tetrahydro-benzo[e][1,4]diazepin-4-yl)-acetylamino]-propionic acid ethyl ester;
3-[2-(1-methyl-7-nitro-2,5-dioxo-1,2,3,5-tetrahydro-benzo[e][1,4]diazepin-4-yl-acetylamino]-propionic acid ethyl ester;
3-[2-[7-(3-benzyl-ureido)-1-methyl-2,5-dioxo-1,2,3,5-tetrahydro-benzo[e][1,4]diazepin-4-yl]-acetylamino]-propionic acid ethyl ester;
3-[2-(7-(N$^2$, N$^3$-bis(tert-butoxycarbonyl)guanidino-1-methyl-2,5-dioxo-1,2,3,5-tetrahydro-benzo[e][1,4]diazepin-4-yl)-acetylamino-propionic acid ethyl ester;
(R,S)-6-(1-methyl-2,5-dioxo-1,2,3,5-tetrahydro-benzo[e][1,4]diazepin-4-yl)-3-phenyl-hexanoic acid ethyl ester;
(R,S)-6-(1-methyl-7-nitro-2,5-dioxo-1,2,3,5-tetrahydro-benzo[e][1,4]diazepin-4-yl)-3-(4-nitro-phenyl)-hexanoic acid ethyl ester;
(R,S)-6-[7-(3-benzyl-ureido)-1-methyl-2,5-dioxo-1,2,3,5-tetrahydro-benzo[e][1,4]diazepin-4-yl]-3-[4-(3-benzyl-ureido)-phenyl]-hexanoic acid ethyl ester;
3-(R,S)-{2-[7-acetylamino-3-(S)-(4-hydroxy-benzyl)-2,5-dioxo-1,2,3,5-tetrahydro-benzo[e][1,4]diazepin-4-yl]-acetylamino}-3-phenyl-propionic acid methyl ester;
3-(R;S)-{2-[7-amino-3-(S)-(4-hydroxy-benzyl)-2,5-dioxo-1,2,3,5-tetrahydro-benzo[e][1,4]diazepin-4-yl]-acetylamino}-3-phenyl-propionic acid methyl ester;
3-(R;S)-{2-[7-amino-3-(S)-(4-hydroxy-benzyl)-2,5-dioxo-1,2,3,5-tetrahydro-benzo[e][1,4]diazepin-4-yl]-acetylamino}-3-phenyl-propionic acid;
3-(R,S)-[2-(7-acetylamino-3-(S)-benzyl-2,5-dioxo-1,2,3,5-tetrahydro-benzo[e][1,4]diazepin-4-yl)-acetylamino]-3-phenyl-propionic acid methyl ester;
3-(R,S)-[2-(7-acetylamino-3-(S,S)-sec-butyl-2,5-dioxo-1,2,3,5-tetrahydro-benzo[e][1,4]diazepin-4-yl)-acetylamino]-3-phenyl-propionic acid methyl ester;
3-(R,S)-{2-[7-acetylamino-3-(S)-(2-methoxycarbonyl-ethyl)-2,5-dioxo-1,2,3,5-tetrahydro-benzo[e][1,4]diazepin-4-yl]-acetylamino}-3-phenyl-propionic acid methyl ester;
3-(R,S)-{2-[7-Amino-3-(S)-benzyl-2,5-dioxo-1,2,3,5-tetrahydro-benzo[e][1,4]diazepin-4-yl]-acetylamino}-butyric acid methyl ester;
3-(R,S)-{2-[7-amino-3-(S)-(4-hydroxy-benzyl)-2,5-dioxo-1,2,3,5-tetrahydro-benzo[e][1,4]diazepin-4-yl]-acetylamino}-butyric acid;
3-(R,S)-[2-(7-amino-3-(S)-isopropyl-2,5-dioxo-1,2,3,5-tetrahydro-benzo[e][1,4]diazepin-4-yl)-acetylamino]-butyric acid;
(R,S)-3-[2-[6-(3-benzyl-ureido)-1-methyl-2,4-dioxo-1,4-dihydro-2H-quinazolin-3-yl]-acetylamino]-3-phenyl-propionic acid);
(1-methyl-6-nitro-2,4-dioxo-1,4-dihydro-2H-quinazolin-3-yl)-acetic acid;
(R,S)-3-[2-(1-methyl-6-nitro-2,4-dioxo-1,4-dihydro-2H-quinazolin-3-yl)-acetylamino]-3-phenyl-propionic acid ethyl ester;
(R,S)-3-[2-(6-amino-1-methyl-2,4-dioxo-1,4-dihydro-2H-quinazolin-3-yl)-acetylamino]-3-phenyl-propionic acid ethyl ester;
(R,S)-3-[2-[6-(3-benzyl-ureido)-1-methyl-2,4-dioxo-1,4-dihydro-2H-quinazolin-3-yl]-acetylamino]-3-phenyl-propionic acid ethyl ester;
(R,S)-3-[2-(6-guanidino-1-methyl-2,4-dioxo-1,4-dihydro-2H-quinazolin-3-yl)-acetylamino]-3-phenyl-propionic acid;
(R,S)-3-[2-(6-(N$^2$, N$^3$-bis(tert-butoxycarbonyl)guanidino-1-methyl-2,4-dioxo-1,4-dihydro-2H-quinazolin-3-yl)-acetylamino]-3-phenyl-propionic acid ethyl ester;
[(2-fluoro-5-nitro-benzoyl)-(2-hydroxy-ethyl)-amino]-acetic acid tert-butyl ester;
(7-nitro-5-oxo-2,3-dihydro-5H-benzo[f][1,4]oxazepin-4-yl)-acetic acid tert-butyl ester;
(7-nitro-5-oxo-2,3-dihydro-5H-benzo[f][1,4]oxazepin-4-yl)-acetic acid;
3-[2-(7-nitro-5-oxo-2,3-dihydro-5H-benzo[f][1,4]oxazepin-4-yl)-acetylamino]-propionic acid ethyl ester;
3-[2-(7-amino-5-oxo-2,3-dihydro-5H-benzo[f][1,4]oxazepin-4-yl)-acetylamino]-propionic acid ethyl ester;
3-{2-[7-(3-benzyl-ureido)-5-oxo-2,3-dihydro-5H-benzo[f][1,4]oxazepin-4-yl]-acetylamino}-propionic acid ethyl ester;
(R,S)-3-[2-(7-nitro-5-oxo-2,3-dihydro-5H-benzo[f][1,4]oxazepin-4-yl)-acetylamino]-3-phenyl-propionic acid ethyl;
(R,S)-3-[2-[7-(3-benzyl-ureido)-5-oxo-2,3-dihydro-5H-benzo[f][1,4]oxazepin-4-yl]-acetylamino]-3-phenyl-propionic acid ethyl ester;
(R,S)-3-{2-[7-(3-benzyl-3-methyl-ureido)-5-oxo-2,3-dihydro-5H-benzo[f][1,4]oxazepin-4-yl]-acetylamino}-3-pyridin-3-yl-propionic acid ethyl ester;
(S)-2-[3-benzyloxycarbonyl-2-[2-(7-nitro-5-oxo-2,3-dihydro-5H-benzo[f][1,4]oxazepin-4-yl)-acetylamino]-propionylamino]-benzoic acid benzyl ester;
(S)-2-[2-[2-(7-amino-5-oxo-2,3-dihydro-5H-benzo[f][1,4]oxazepin-4-yl)-acetylamino]-3-carboxy-propionyl-amino]-benzoic acid;
(R,S)-3-[2-(7-nitro-5-oxo-2,3-dihydro-5H-benzo[f][1,4]oxazepin-4-yl)-acetylamino]-3-pyridin-3-yl-propionic acid ethyl ester;
(R,S)-3-{2-[7-(3-butyl-ureido)-5-oxo-2,3-dihydro-5H-benzo[f][1,4]oxazepin-4-yl]-acetylamino}-3-pyridin-3-yl-propionic acid ethyl ester;
(R,S)-3-(2-{7-[3-(4-fluoro-benzyl)-ureido]-5-oxo-2,3-dihydro-5H-benzo[f][1,4]oxazepin-4-yl}-acetylamino)-3-pyridin-3-yl-propionic acid ethyl ester;
(R,S)-[(2-fluoro-5-nitro-benzoyl)-(2-hydroxy-2-phenyl-ethyl)-amino]-acetic acid tert-butyl ester;
(R,S)-(7-nitro-5-oxo-2-phenyl-2,3-dihydro-5H-benzo[f][1,4]oxazepin-4-yl)-acetic acid tert-butyl ester;

(R,S)-3-[2-(7-nitro-5-oxo-2-phenyl-2,3-dihydro-5H-benzo[f][1,4]oxazepin-4-yl)-acetylamino]-3-phenyl-propionic acid ethyl ester;

(R,S)-3-{2-[7-(3-benzyl-ureido)-5-oxo-2-phenyl-2,3-dihydro-5H-benzo[f][1,4]oxazepin-4-yl]-acetylamino}-3-phenyl-propionic acid ethyl ester;

6-(7-acetylamino-2,5-dioxo-1,2,3,5-tetrahydro-benzo[e][1,4]diazepin-4-yl)-hexanoic acid methyl ester;

(R,S)-6-[7-acetylamino-2,5-dioxo-1,2,3,5-tetrahydro-benzo[e][1,4]diazepin-4-yl]-3-phenyl-hexanoic acid ethyl ester.

The compounds of formula I described above for use as therapeutically active substances are a further object of the invention.

Also an object of the invention are compounds described above for the production of medicaments for the prophylaxis and therapy of illnesses which are caused by a malfunction of the binding of adhesive proteins to vitronectin receptors.

Likewise an object of the invention are pharmaceutical compositions containing a compound of formula I described above and a therapeutically inert carrier. The invention likewise relates to a pharmaceutical composition as previously described, which additionally contains one or more compounds of formula I or additionally one or more compounds selected from the group comprising anticoagulants, fibrinolytics as well as medicaments for the prophylaxis and therapy of illnesses which are caused by a malfunction of the binding of adhesive proteins to vitronectin receptors.

An object of the invention is also the use of the compounds described above for the production of medicaments, particularly for the treatment or prophylaxis of illnesses which are caused by a malfunction of the binding of adhesive proteins to vitronectin receptors.

Also an object of the invention is the use of one of the compounds described above for the production of medicaments e.g. for the treatment or prophylaxis of neoplasms, tumor metastasing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi.

A further object of the invention comprises compounds which are manufacturable according to one of the described processes.

Likewise an object of the invention are methods for the treatment and prophylaxis of illnesses which are caused by a malfunction of the binding of adhesive proteins to vitronectin receptors and which are comprised by the administration of an effective amount of a compound of formula I.

A further object of the invention is a method for the treatment and phophylaxis of neoplasms, tumor metastasing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi, whereby an effective amount of one of the compounds described above is administered.

Likewise an object of the invention are compounds described above for the treatment and prophylaxis of neoplasms, tumor metastasing, tumor growth, osteoporosis, Paget's disease, diabetic retinopathy, macular degeneration, restenosis following vascular intervention, psoriasis, arthritis, fibrosis, kidney failure as well as infection caused by viruses, bacteria or fungi.

The conversion of a compound of formula I into a pharmaceutically usable salt can be carried out by treatment of such a compound with an inorganic acid, for example a hydrohalic acid, such as, for example, hydrochloric acid or hydrobromic acid, sulphuric acid, nitric acid, phosphoric acid etc., or with an organic acid, such as, for example, acetic acid, citric acid, maleic acid, fumaric acid, tartaric acid, methanesulphonic acid or p-toluenesulphonic acid.

The corresponding carboxylate salts can also be prepared from the compounds of formula I by treatment with physiologically compatible bases.

The conversion of a compound of formula I into a pharmaceutically usable ester can be accomplished by treatment of such a compound in the usual way e.g. with an alcohol in the presence of a catalytic amount of an acid like p-TsOH.

As mentioned previously, the compounds of formula I and their pharmaceutically usable salts inhibit especially the binding of various adhesive proteins such as fibrinogen, vitronectin, von Willebrand factor, fibronectin, thrombospondin and osteopontin to the vitronectin receptors (such as e.g. $\alpha_v\beta_3$, $\alpha_v\beta_5$, $\alpha_v\beta_6$, $\alpha_v\beta_8$, etc.) on the surface of different types of cells. The said compounds therefore influence cell-cell and cell-matrix interactions. Since the vitronectin receptors play a role, inter alia, in the spread of tumor cell, in vascular regeneration, in the degradation of bone tissue, in the migration of smooth muscle cells in vascular walls and in the invasion of virus particles into target cells, the said compounds can be used as vitronectin receptor antagonists in the control or prevention of neoplasms, tumor metestasis, osteoporosis, Paget's disease, diabetic retinopathy, macular degeneration, restenosis following vascular intervention, psoriasis, arthritis, kidney failure as well as infections caused by viruses, bacteria or by fungi. Since the binding of the adhesive proteins to the fibrinogen receptor ($\alpha_{IIb}\beta_3$) on the surface of blood platelets is practically not inhibited, undesired side effects, such as e.g. bleeding, can be suppressed with the therapeutic application of the said compounds.

The inhibition of the binding of adhesive proteins such as e.g. fibrinogen to vitronectin receptors (such as e.g. $\alpha_v\beta_3$, $\alpha_v\beta_5$, $\alpha_v\beta_6$, $\alpha_v\beta_8$, etc.) by compounds of the present invention can be determined as described by L. Alig et al. (J. Med. Chem. 1992, 35, 4393–4407).

In detail thereto, the wells of microtiter plates (Nunc-Immunoplate MaxiSorp) were coated overnight at 4° C. with the vitronectin receptor $\alpha_v\beta_3$ (from human placenta, 100 µl/well) in a buffer system with 150 mmol/l NaCl, 1 mmol/CaCl$_2$, 1 mmol/l MgCl$_2$, 0.0005% Triton X-100 and 20 mmol/l Tris HCl, pH 7.4. The non-specific binding sites were blocked by incubation with 3.5% bovine serum albumin (BSA from Fluka) at 20° C. for at least 1 h. Before the beginning of the test the plates were washed in each case once with 150 mmol/l NaCl, 1 mmol/l CaCl$_2$, 1 mmol/l MgCl$_2$ and 20 mmol/l Tris HCl, pH 7.4 (buffer A). The thus-coated plates can be stored for at least 2 months in the presence of 0.05% NaN$_3$ (in buffer A) at 4° C. in a humidity chamber without loss of binding activity. Fibrinogen (IMCO, free from fibronectin) was diluted to 1.5 µg/ml in buffer A in the presence of 1% BSA. The wells coated with the receptor were incubated with fibrinogen (100 µl/well) overnight at room temperature in the absence of or in the presence of increasing concentrations of RGDS (as the reference substance) or the compounds to be measured. Non-bound fibrinogen was removed by three-fold washing with buffer A, bound fibrinogen was detected by an ELISA procedure. Antibodies of rabbits directed against human fibrinogen (Dakopatts, Denmark), diluted in buffer A in the presence of 0.1% BSA, were added at room temperature for 1 h, followed by incubation with biotinylated antibodies directed against rabbit immunoglobulin (Amersham) for 30 min. Non-bound antibodies were removed by three-fold washing with buffer A. Thereafter, the pre-formed streptavidin-biotinylated peroxidase complex (Amersham) was added for 30 min. Three-fold washing with buffer A was again carried out. After addition of the peroxidase substrate ABTS (2,2'-azino-bis(3-ethylbenzothiazoline-6-sulphonic acid), Boehringer Mannheim) the enzyme activity was measured with a multichannel photometer (UVmax, Molecular Devices). The difference between total binding activity (in the absence of a test substance) and non-specific binding activity (in the presence of 100 μM RGDS) is taken as the specific binding activity.

The concentration of a test substance which is required to inhibit the specific binding activity by 50% was defined as the $IC_{50}$.

The isolation of the receptor $\alpha_v\beta_3$ used in the test can be carried out as follows: Human placenta is stored at –80° C. immediately after its excision. In order to extract the receptor, each placenta is superficially thawed and cut into narrow strips with a scalpel. The pieces are washed twice with a buffer of 150 mmol/l NaCl, 1 mmol/l $CaCl_2$, 1 mmol/l $MgCl_2$ and 20 mmol/l Tris HCl (pH 7.4). The proteins are extracted at room temperature for one hour with a buffer solution from 1% Triton X-100, 150 mmol/l NaCl, 1 mmol/l $CaCl_2$, 1 mmol/l $MgCl_2$, 20 mmol/l Tris HCl, 0.02% $NaN_3$, 0.5 mmol/l phenylmethane-sulphonyl fluoride, 1 mmol/l leupeptin and 2 mmol/l N-ethylmaleimide (pH 7.4) and filtered through sterile gauze. The filtrate is centrifuged at 30000 g for 30 min. at 4° C. The glycoproteins are firstly separated with the aid of a concanavalin A-Sepharose 4B column. The proteins bound to the column are eluted and then added to a Aeg-RGDS column. After repeated washing the bound vitronectin receptor is eluted by 3 mmol/l RGDS in a buffer of 0.1% Triton X-100, 150 mmol/l NaCl, 20 mmol/l Tris HCl, 1 mmol/l $CaCl_2$, 1 mmol/l $MgCl_2$, 0.05% $NaN_3$ (pH 7.0).

In the listings of specific compounds of formula I above, preferred compounds have $IC_{50}$ values below 1000 nM and particularly preferred compounds have $IC_{50}$ values below 10 nM. These results have been obtained by using the foregoing test.

The compounds of formula I and their pharmaceutically usable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically usable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragees and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically usable salts and esters can be used as vitronectin receptor antagonists especially for the treatment or prophylaxis of neoplasms, tumor metastasing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1–3 individual doses, which can consist, for example, of the same amounts, should be appropriate. It will, however, be clear that the upper limit given above can be exceeded when this is shown to be indicated.

The disclosure of European Patent Application No. 99113708.4, filed Jul. 13, 1999, is incorporated herein by reference.

The invention is illustrated hereinafter by Examples, which have no limiting character.

EXAMPLE 1

To a solution of (R,S)-3-[2-[7-(3-benzyl-ureido)-1-methyl-2,5-dioxo-1,2,3,5-tetrahydro-benzo[e][1,4]diazepin-4-yl]-acetylamino]-3-phenyl-propionic acid ethyl ester (400 mg, 0.7 mmol) in EtOH (5 ml) was added an aqueous solution of LiOH (1 N, 2 ml). The reaction mixture was kept at 50° C. until no starting material could be detected by TLC. The reaction mixture was neutralized by addition of aqueous HCl and the precipitate formed was collected by filtration, washed with water and dried to give (R,S)-3-[2-[7-(3-benzyl-ureido)-1-methyl-2,5-dioxo-1,2,3,5-tetrahydro-benzo[e][1,4]diazepin-4-yl]-acetylamino]-3-phenyl-propionic acid (340 mg): mp. 151–153° C.; MS (ISP): 544 $(M+H)^+$.

The starting material was prepared as follows: (for a related reaction sequence see e.g. B. K. Blackburn et al., J. Med. Chem. 1997, 40, 717–729)

a) To a slurry of glycine ethyl ester hydrochloride (3.5 g, 25 mmol) in dichloromethane (30 ml) was added triethylamine (3.44 ml, 25 mmol) and N-methylisatoic acid anhydride (3.5 g, 20 mmol). After stirring overnight the reaction mixture was washed with water and the organic layer transferred to a round bottomed flask. To this solution was added water (30 ml) followed by bromoacetyl bromide (2.9 ml, 33 mmol). The resulting emulsion was vigorously stirred and neutralized by addition of a saturated aqueous solution of $Na_2CO_3$. The organic layer was separated and dried over $Na_2SO_4$. After filtration into a round bottomed flask DBU (4.45 ml, 30 mmol) was added to the filtrate. After stirring for 1 h at room temperature the reaction mixture was washed once with aqueous $KHSO_4$ (0.1 N) and twice with aqueous HCl (1N). The aqueous extracts were washed with dichloromethane. The combined organic extracts were dried over Na$_2$SO$_4$, filtered and the solvents evaporated to give (1-methyl-2,5-dioxo-1,2,3,5-tetrahydro-benzo[e][1,4]diazepin-4-yl)-acetic acid ethyl ester as a brown oil (5.1 g): MS (EI): 276 (M)$^+$.

b) To conc H$_2$SO$_4$ (14 ml), kept in an ice bath, KNO$_3$ (2 g, 20 mmol) was added in portions whereby the temperature rose to 10° C. (see also R. I. Fryer et al., J. Heterocyclic Chem. 1991, 28, 1203–1208). To this mixture was added a solution of (1-methyl-2,5-dioxo-1,2,3,5-tetrahydro-benzo[e][1,4]diazepin-4-yl)-acetic acid ethyl ester (5 g, 18 mmol) in dichloromethane (16 ml) whereby the temperature was kept between 20–25° C. After stirring for 90 min the mixture was carefully poured onto ice water and extracted with dichloromethane. The organic extracts were washed with aqueous sat. NaHCO$_3$ followed by water, dried over Na$_2$SO$_4$ and the solvents evaporated. Upon addition of EtOH to the oily residue a precipitate was formed which was collected by filtration to give (1-methyl-7-nitro-2,5-dioxo-1,2,3,5-tetrahydro-benzo[e][1,4]diazepin-4-yl)-acetic acid ethyl ester (4 g): mp. 129–130° C.; MS (EI): 321 (M)$^+$.

c) To a solution of (1-methyl-7-nitro-2,5-dioxo-1,2,3,5-tetrahydro-benzo[e][1,4]diazepin-4-yl)-acetic acid ethyl ester (3.21 g, 10 mmol) in MeCN(15 ml) was added triethylamine (5.85 ml, 42.5 mmol). After cooling of this mixture to about 5° C. Pd—C (10%, 200 mg) and a solution of formic acid (1.6 ml) in MeCN(2 ml) were added. The ice bath was removed, gas evolution started and the temperature of the reaction mixture rose to 35° C. After 1 h the reaction mixture was heated to reflux temperature until all starting material had disappeared according to TLC. After filtration, evaporation of the solvents, and chromatography (silica gel, dichloromethane/MeOH 19:1) (7-amino-1-methyl-2,5-dioxo-1,2,3,5-tetrahydro-benzo[e][1,4]diazepin-4-yl)-acetic acid ethyl ester (1.9 g) was isolated: mp. 118–119° C.; MS (EI): 291 (M)$^+$.

d) To a solution of (7-amino-1-methyl-2,5-dioxo-1,2,3,5-tetrahydro-benzo[e][1,4]diazepin-4-yl)-acetic acid ethyl ester (0.65 g, 2.23 mmol) in DMF (5 ml) was added benzylisocyanate (0.5 g, 3.75 mmol) and DMAP (5 mg). After 2 h at 60° C. the reaction mixture was poured into AcOEt (70 ml), washed with aqueous KHSO$_4$ (0.1 N) and water. After drying over Na$_2$SO$_4$ and evaporation of the solvents the residue was purified by chromatography (dichloromethane/MeOH 19:1) to give [7-(3-benzyl-ureido)-1-methyl-2,5-dioxo-1,2,3,5-tetrahydro-benzo[e][1,4]diazepin-4-yl]-acetic acid ethyl ester (930 mg, 2.19 mmol): mp. 151° C.; MS (EI): 424 (M)$^+$.

e) To solution of [7-(3-benzyl-ureido)-1-methyl-2,5-dioxo-1,2,3,5-tetrahydro-benzo[e][1,4]diazepin-4-yl]-acetic acid ethyl ester (850 mg, 2 mmol) in EtOH (10 ml) was added aqueous LiOH (1 N, 4 ml). After 1 h at room temperature the reaction mixture was acidified to pH 4 by addition of 2 N HCl$_{aq}$ and the solvents evaporated. Upon addition of water followed by AcOEt crystallization was induced to give, after drying, [7-(3-benzyl-ureido)-1-methyl-2,5-dioxo-1,2,3,5-tetrahydro-benzo[e][1,4]diazepin-4-yl]-acetic acid (800 mg, 2 mmol): mp. 182° C.; MS (ISP): 397 (M+1)$^+$.

f) To a solution of [7-(3-benzyl-ureido)-1-methyl-2,5-dioxo-1,2,3,5-tetrahydro-benzo[e][1,4]diazepin-4-yl]-acetic acid (396 mg, 1 mmol) in DMF (5 ml) was subsequently added DIPEA (0.3 ml), (R,S)-3-amino 3-phenylpropanoic acid ethyl ester (276 mg, 1.2 mmol, obtained by esterification of the corresponding acid, see e.g. P. Kuehne et al, Helv. Chim. Acta 1996, 79, 1085–94), and BOP (500 mg, 1.2 mmol). After stirring overnight at RT the reaction mixture was extracted with AcOEt. The organic extracts were washed with HCl$_{aq}$ (0.5 N), water, and saturated aqueous NaHCO$_3$. After drying over Na$_2$SO$_4$ and evaporation of the solvents (R,S)-3-[2-[7-(3-benzyl-ureido)-1-methyl-2,5-dioxo-1,2,3,5-tetrahydro-benzo[e][1,4]diazepin-4-yl]-acetylamino]-3-phenyl-propionic acid ethyl ester (450 mg, 0.79 mmol) was isolated: mp. 114–117° C.; MS (ISP): 571 (M+1)$^+$.

EXAMPLE 2

To a solution of (R,S)-3-[2-(7-(N$^2$, N$^3$-bis(tert-butoxycarbonyl)guanidino-1-methyl-2,5-dioxo-1,2,3,5-tetrahydro-benzo[e][1,4]diazepin-4-yl)-acetylamino]-3-phenyl-propionic acid ethyl ester (210 mg, 0.3 mmol) in dichloromethane (3 ml) was added TFA (0.75 ml). After 2 h at 35° C. the solvents were evaporated and the residue dissolved in EtOH (3 ml). After addition of aqueous LiOH (1 N, 1.5 ml) the reaction mixture was kept at 80° C. for 2 h. Evaporation of the solvents, addition of water, neutralization with HCl$_{aq}$ (2 N) followed by addition of AcOEt/EtOH yielded a precipitate which was collected by filtration to give after drying (R,S)-3-[2-(7-Guanidino-1-methyl-2,5-dioxo-1,2,3,5-tetrahydro-benzo[e][1,4]diazepin-4-yl)-acetylamino]-3-phenyl-propionic acid hydrochloride (80 mg, 0.164 mmol): mp. 245–250° C.; MS (ISP): 453 (M+1)+, 471 (M+NH$_4$)$^+$.

The starting material was prepared as follows:

a) To a solution of (7-amino-1-methyl-2,5-dioxo-1,2,3,5-tetrahydro-benzo[e][1,4]diazepinyl)-acetic acid ethyl ester (1.46 g, 5 mmol, Example 1c) and pyridine (0.8 ml) in ethylenchloride/DMF 3:2 (12.5 ml) was added N,N'-bis(tert-butoxycarbonyl)-S-methylisothiourea (1.45 g, 5 mmol, R. J. Bergeron et al. J. Org. Chem. 1987, 52, 1700–1703) followed by Hg(OAc)$_2$ (0.8 g, 2.5 mmol). After stirring for 20 h at RT, whereby a thick precipitate was formed, the reaction mixture was distributed between dichloromethane and water and acidified by addition of 2 N HCl. The organic extracts were washed with water, dried, and evaporated. The residue was recrystallized from EtOH to give (7-N$^2$, N$^3$-bis(tert-butoxycarbonyl)guanidino-1-methyl-2,5-dioxo-1,2,3,5-tetrahydro-benzo[e][1,4]diazepin-4-yl)-acetic acid ethyl ester (1.65 g, 3.1 mmol): mp. 166° C.(dec.); MS (ISP): 534 (M+1)$^+$.

b) To a suspension of (7-N$^2$, N$^3$-bis(tert-butoxycarbonyl)guanidino-1-methyl-2,5-dioxo-1,2,3,5-tetrahydro-benzo[e][1,4]diazepin-4-yl)-acetic acid ethyl ester (1.6 g, 3 mmol) in EtOH/water 1:1 (30 ml) was added K$_2$CO$_3$ (1.5 g). The reaction mixture was stirred at 60° C. for 1 h whereby a yellow solution was formed. The mixture was then cooled to about 5° C., diluted with water, and carefully acidified to pH 3 upon addition of 2 N HCl$_{aq}$. The precipitate formed was collected by filtration, washed with water, and dried to give (7-N$^2$, N$^3$-bis(tert-butoxycarbonyl)guanidino-1-methyl-2,5-dioxo-1,2,3,5-tetrahydro-benzo[e][1,4] diazepin-4-yl)-acetic acid (530 mg, 1.05 mmol): mp. >250° C.(dec.); MS (ISP): 506 (M+1)$^+$.

c) A solution of (7-N$^2$, N$^3$-bis(tert-butoxycarbonyl)guanidino-1-methyl-2,5-dioxo-1,2,3,5-tetrahydro-benzo[e][1,4]diazepin-4-yl)-acetic acid (253 mg, 0.5 mmol), (R,S)-3-amino-3-phenyl-propanoic acid ethyl ester (126 mg, 0.55 mmol), EEDQ (240 mg, 1 mmol), and NEt$_3$ (0.2 ml) in dichloromethane was stirred for 3 h at 40 ° C. After usual work-up (see Example 1f) and purification by chromatography (SiO$_2$, dichloromethane/MeOH 49:1) (R,S)-3-[2-(7-(N$^2$, N$^3$M-bis(tert-butoxycarbonyl)

guanidino-1-methyl-2,5-dioxo-1,2,3,5-tetrahydro-benzo[e][1,4]diazepin-4-yl)-acetylamino]-3-phenyl-propionic acid ethyl ester (230 mg, 0.33 mmol) was obtained: mp. 115–116° C.(dec.); MS (ISP): 681 (M+l)$^+$.

EXAMPLE 3

From 3-[2-[7-(3-benzyl-ureido)-1-methyl-2,5-dioxo-1,2,3,5-tetrahydro-benzo[e][1,4]diazepin-4-yl]-acetylamino]-propionic acid ethyl ester (250 mg, 0.5 mmol) the corresponding acid, 3-[2-[7-(3-benzyl-ureido)-1-methyl-2,5-dioxo-1,2,3,5-tetrahydro-benzo[e][1,4]diazepin-4-yl]-acetylamino]-propionic acid ( 160 mg, 0.34 mmol), was obtained by the same procedure as described in Example 1: mp. 116° C.(dec.); MS (ISP): 468 (M+1)$^+$. The starting material was prepared as follows:
a) Using glycyl-β-alanine ethyl ester hydrochloride (R. Kobayashi and S. Ishii, J. Biochem. (Tokyo) (1974), 75(4), 825–35) and the experimental protocol described in Example 1 a) 3-[2-(1-methyl-2,5-dioxo-1,2,3,5-tetrahydro-benzo[e][1,4]diazepin-4-yl)-acetylamino]-propionic acid ethyl ester was obtained: mp. 110–112° C.; MS (ISP): 348 (M+1)$^+$.
b) Nitration of 3-[2-(1-methyl-2,5-dioxo-1,2,3,5-tetrahydro-benzo[e][1,4]diazepin-4-yl)-acetylamino]-propionic acid ethyl ester as described in Example 1b) yielded 3-[2-(1-methyl-7-nitro-2,5-dioxo-1,2,3,5-tetrahydro-benzo[e][1,4]diazepin-4-yl)-acetylamino]-propionic acid ethyl ester as a pale yellow resin: MS (ISP): 393 (M+1)$^+$.
c) Catalytic hydrogenation of 3-[2-(1-methyl-7-nitro-2,5-dioxo-1,2,3,5-tetrahydro-benzo[e][1,4]diazepin-4-yl)-acetylamino]-propionic acid ethyl ester in EtOH in the presence of 10% Pd/C at RT and atmospheric pressure followed by acylation with benzylisocyanate as described in Example 1d) gave 3-[2-[7-(3-benzyl-ureido)-1-methyl-2,5-dioxo-1,2,3,5-tetrahydro-benzo[e][1,4]diazepin-4-yl]-acetylamino]-propionic acid ethyl ester: mp. 100–102° C.; MS (ISP): 496 (M+1)$^+$.

EXAMPLE 4

Treatment of 3-[2-(7-(N$^2$, N$^3$-bis(tert-butoxycarbonyl)guanidino-1-methyl-2,5-dioxo-1,2,3,5-tetrahydro-benzo[e][1,4]diazepin-4-yl)-acetylamino-propionic acid ethyl ester with TFA in dichloromethane followed by hydrolysis of the obtained intermediate with LiOH as described in Example 2 provided 3-[2-(7-guanidino-1-methyl-2,5-dioxo-1,2,3,5-tetrahydro-benzo[e][1,4]diazepin-4-yl)-acetylamino]-propionic acid hydrochloride: mp. 126° C.; MS (ISP): 377 (M+1)$^+$.

The starting material was prepared as follows:

Coupling of (7-N$^2$, N$^3$-bis(tert-butoxycarbonyl)guanidino-1-methyl-2,5-dioxo-1,2,3,5-tetrahydro-benzo[e][1,4]diazepin-4-yl)-acetic acid (253 mg, 0.5 mmol; Example 2b) with 3-amino-propionic acid ethyl ester hydrochloride (85 mg, 0.55 mmol) in dichloromethane in the presence of NEt$_3$ and EEDQ as described in Example 2c) gave after usual work-up and chromatography on silica gel (dichloromethane/MeOH 49:1) 3-[2-(7-(N$^2$, N$^3$-bis(tert-butoxycarbonyl)guanidino-1-methyl-2,5-dioxo-1,2,3,5-tetrahydro-benzo[e][1,4]diazepin-4-yl)-acetylamino-propionic acid ethyl ester (195 mg, 0.32 mmol): mp. 176° C.(dec.); MS (ISP): 605 (M+1)$^+$.

EXAMPLE 5

Hydrolysis of (R,S)-6-[7-(3-benzyl-ureido)-1-methyl-2,5-dioxo-1,2,3,5-tetrahydro-benzo[e][1,4]diazepin-4-yl]-3-[4-(3-benzyl-ureido)-phenyl]-hexanoic acid ethyl ester (210 mg, 0.3 mmol) with LiOH in EtOH/water as described in Example 1 yielded (R,S)-6-[7-(3-Benzly-ureido)-1-methyl-2,5-dioxo-1,2,3,5-tetrahydro-benzo[e][1,4]diazepin-4-yl]-3-[4-(3-benzyl-ureido)-phenyl]-hexanoic acid (120 mg, 0.18 mmol): mp. 155–160° C.(dec.); MS (ISP): 677 (M+1)$^+$.

The starting material was prepared as follows:
a) Using (R,S)-6-amino-3-phenyl-hexanoic acid ethyl ester hydrochloride (Eur. Pat. Appl. No. 98100006.0, filing date Jan. 2, 1998) and the experimental protocol described in Example 1 a) (R,S)-6-(1-methyl-2,5-dioxo-1,2,3,5-tetrahydro-benzo[e][1,4]diazepin-4-yl)-3-phenyl-hexanoic acid ethyl ester was obtained as a brownish oil; MS (ISP): 409 (M+1)$^+$.
b) Nitration of (R,S)-6-(1-methyl-2,5-dioxo-1,2,3,5-tetrahydro-benzo[e][1,4]diazepin-4-yl)-3-phenyl-hexanoic acid ethyl ester as described in Example 1b) yielded (R,S)-6-(1-methyl-7-nitro-2,5-dioxo-1,2,3,5-tetrahydro-benzo[e][1,4]diazepin-4-yl)-3-(4-nitro-phenyl)-hexanoic acid ethyl ester as a pale yellow foam; MS (ISP): 499 (M+1)$^+$.
c) Catalytic hydrogenation followed by reaction with benzylisocyanate as described in Example 3c) gave (R,S)-6-[7-(3-benzyl-ureido)-1-methyl-2,5-dioxo-1,2,3,5-tetrahydro-benzo[e][1,4]diazepin-4-yl]-3-[4-(3-benzyl-ureido)-phenyl]-hexanoic acid ethyl ester as a colorless foam; MS (ISP): 705 (M+1)$^+$.

EXAMPLE 6

To a solution of 3-(R,S)-{2-[7-amino-3-(S)-(4-hydroxy-benzyl)-2,5-dioxo-1,2,3,5-tetrahydro-benzo[e][1,4]diazepin-4-yl]-acetylamino}-3-phenyl-propionic acid (0.1 mmol, 50mg) in DMF (2.5 mL) was added benzylisocyanate (31 μl 0.25 mmol). The mixture was shaken at 45° C. over night until no starting material was detected by HPLC. Afterwards the solution was concentrated in vacuo. The crude product was purified by RP-HPLC to give 3-(R,S)-{2-[7-(3-benzyl-ureido)-3-(S)-(4-hydroxy-benzyl)-2,5-dioxo-1,2,3,5-tetrahydro-benzo[e][1,4]diazepin-4-yl]-acetylamino}-3-phenyl-propionic acid (20 mg): MS 634 (M–H)$^-$.

The starting material was prepared as follows:
a) To a solution of H-Tyr(tBut)-OMe HCl (0.863 mg, 3 mmol) in methanol (7 ml) and DMF (1.5 ml), there was added DIPEA (0.51 ml; 3 mmol), formaldehyde (aqueous 36%, 0.23 ml,3 mmol), 5-N-acetylamino-2-azidobenzoic acid (660 mg;3 mmol), as well as 3-isocyano-3-phenylpropionic acid (567 mg; 3 mmol). This mixture was stirred over night at RT. The solution was evaporated and purified by filtration over a pad of silicagel to give 2-{(5-acetylamino-2-azido-benzoyl)-(R,S)-[(2-methoxycarbonyl-1-phenyl-ethylcarbamoyl)-methyl]-amino}-3-(S)-(4-tert-butoxy-phenyl)-propionic acid methyl ester(1.28 g): MS 673 (M+H)$^+$.
b) To a solution of 2-{(5-acetylamino-2-azido-benzoyl)-(R,S)-[(2-methoxycarbonyl-1-phenyl-ethylcarbamoyl)-methyl]-amino}-3-(S)-(4-tert-butoxy-phenyl)-propionic acid methyl ester (672 mg, 1 mmol) in dry 1,2-dichlorethane (10 ml) there was added polymer bound triphenylphosphine (600 mg,1.8 mmol). The suspension was shaken at 40° C. for 4 h. The resin was collected and washed with 1,2-dichlorethane/acetonitrile(1:1) for 5 times. The resin was taken up in 90% aqueous acetic acid and heated to 110° C. for 32 h. The reaction mixture was filtered and the filtrate was purified by RP-HPLC to give 60 mg of 3-(R,S)-{2-[7-acetylamino-3-(S)-(4-hydroxy-benzyl)-2,5-dioxo-1,2,3,5-tetrahydro-benzo[e][1,4]diazepin-4-yl]-acetylamino}-3-phenyl-propionic acid methyl ester. MS: 559 (M+H)$^+$.

c) A solution of 3-(R,S)-{2-[7-acetylamino-3-(S)-(4-hydroxy-benzyl)-2,5-dioxo-1,2,3,5-2tetrahydro-benzo[e][1,4]diazepin-4-yl]-acetylamino}-3-phenyl-propionic acid methyl ester (55 mg, 0.1 mmol) in methanol/thionyl chloride (100:1, 4 ml ) was stirred at RT over night. The reaction mixture was evaporated to give 3-(R;S)-{2-[7-amino-3-(S)-(4-hydroxy-benzyl)-2,5-dioxo-1,2,3,5-tetrahydro-benzo[e][1,4]diazepin-4-yl]-acetylamino}-3-phenyl-propionic acid methyl ester (50mg): MS (ISP) 517 (M+H)$^+$.

d) To a solution of 3-(R,S)-{2-[7-amino-3-(S)-(4-hydroxy-benzyl)-2,5-dioxo-1,2,3,5-tetrahydro-benzo[e][1,4]diazepin-4-yl]-acetylamino}-3-phenyl-propionic acid methyl ester (50mg, 0.09 mmol) in THF/methanol (3:1, 4ml) was added 1N aqueous NaOH (0.8ml). The reaction was stirred at RT over night. The solution was neutralised with 1N aqueous HCl, and evaporated to dryness to give 3-(R;S)-{2-[7-amino-3-(S)-(4-hydroxy-benzyl)-2,5-dioxo-1,2,3,5-tetrahydro-benzo[e][1,4]diazepin-4-yl]-acetylamino}-3-phenyl-propionic acid. MS: (M–H)$^-$ 501.

EXAMPLE 7

To a solution of 3-(R;S)-{2-[7-amino-3-(S)-benzyl-2,5-dioxo-1,2,3,5-tetrahydro-benzo[e][1,4]diazepin-4-yl]-acetylamino}-3-phenyl-propionic acid (0.134 mmol, 65 mg) in DMF (2.5 ml) there was added benzylisocyanate (40 µl 0.33 mmol). The mixture was shaken at 45° C. until no starting material was detectable. The solution was evaporated and the crude product was purified by RP-HPLC to give 3-(R;S)-{2-[7-(3-Benzyl-ureido)-3-(S)-benzyl-2,5-dioxo-1,2,3,5-tetrahydro-benzo[e][1,4]diazepin-4-yl]-acetylamino}-3-phenyl-propionic acid (13 mg): MS 618 (M–H)$^-$.

The starting material was prepared as follows:

a) 2-(R,S)-{(5-acetylamino-2-azido-benzoyl)-[(2-methoxycarbonyl-1-phenyl-ethylcarbamoyl)-methyl]-amino}-3-(S)-phenyl-propionic acid methyl ester: MS (ISP) 601 (M+H)$^+$; prepared as described in Example 6a).

b) 3-(R,S)-[2-(7-acetylamino-3-(S)-benzyl-2,5-dioxo-1,2,3,5-tetrahydro-benzo[e][1,4]diazepin-4-yl)-acetylamino]-3-phenyl-propionic acid methyl ester: MS 543 (M+H)$^+$; prepared as described in Example 6b).

c) 3-(R,S)-[2-(7-amino-3-(S)-benzyl-2,5-dioxo-1,2,3,5-tetrahydro-benzo[e][1,4]diazepin-4-yl)-acetylamino]-3-phenyl-propionic acid methyl ester: MS 518 (M+NH$_4$)$^+$; prepared as described in Example 6c).

d) 3-(R,S)-[2-(7-amino-3-(S)-benzyl-2,5-dioxo-1,2,3,5-tetrahydro-benzo[e][1,4]diazepin-4-yl)-acetylamino]-3-phenyl-propionic acid: MS 504 (M+NH$_4$)$^+$; MS 485 (M–H)$^-$; prepared as described in Example 6d).

EXAMPLE 8

To a solution of 3-(R;S)-{2-[7-amino-3-(S,S)-sec-butyl-2,5-dioxo-1,2,3,5-tetrahydro-benzo[e][1,4]diazepin-4-yl]-acetylamino}-3-phenyl-propionic acid (0.11 mmol, 50mg) in DMF (2.5 ml) was added benzylisocyanate (30 µl 0.25 mmol). The mixture was shaken at 45° C. until no starting material was detectable. The solution was evaporated and the crude product was purified by RP-HPLC to give 3-(R,S)-{2-[7-(3-benzyl-ureido)-(3-(S,S)-sec-butyl-2,5-dioxo-1,2,3,5-tetrahydro-benzo[e][1,4]diazepin-4-yl]-acetylamino}-3-phenyl-propionic acid (16 mg): MS (ISN) 584 (M–H)$^-$.

The starting material was prepared as follows:

a) 2-(S,S)-{(5-acetylamino-2-azido-benzoyl)-(R,S)-[(2-methoxycarbonyl-1-phenyl-ethylcarbamoyl)-methyl]-amino}-3-methyl-pentanoic acid methyl ester: MS (ISP) 567 (M+H)$^+$; prepared as described in Example 6a).

b) 3-(R,S)-[2-(7-acetylamino-3-(S,S)-sec-butyl-2,5-dioxo-1,2,3,5-tetrahydro-benzo[e][1,4]diazepin-4-yl)-acetylamino]-3-phenyl-propionic acid methyl ester: MS (ISP) 509 (M+H)$^+$; prepared as described in Example 6b).

c) 3-(R,S)-[2-(7-amino-3-(S,S)-sec-butyl-2,5-dioxo-1,2,3,5-tetrahydro-benzo[e][1,4]diazepin-4-yl)-acetylamino]-3-phenyl-propionic acid methyl ester: MS 484 (M+NH$_4$)$^+$; prepared as described in Example 6c).

d) 3-(R,S)-[2-(7-amino-3-(S,S)-sec-butyl-2,5-dioxo-1,2,3,5-tetrahydro-benzo[e][1,4]diazepin-4-yl)-acetylamino]-3-phenyl-propionic acid: MS (ISN) 451 (M–H)$^-$; prepared as described in Example 6d).

EXAMPLE 9

To a solution of 3-(R,S)-{2-[7-amino-3-(S)-(2-carboxy-ethyl)-2,5-dioxo-1,2,3,5-tetrahydro-benzo[e][1,4]diazepin-4-yl]-acetylamino}-3-phenyl-propionic acid (0.15 mmol, 70 mg) in DMF (2.5 ml) was added benzylisocyanate (46 µl, 037 mmol). The mixture was shaken at 45° C. over night. Then the solution was evaporated and the crude product was purified by RP-HPLC to give 3-(R,S)-{2-[7-(3-benzyl-ureido)-3-(S)-(2-carboxy-ethyl)-2,5-dioxo-1,2,3,5-tetrahydro-benzo[e][1,4]diazepin-4-yl]-acetylamino}-3-phenyl-propionic acid (14 mg): MS (ISN) 600 (M–H)$^-$.

The starting material was prepared as follows.

a) 2-(S)-{(5-acetylamino-2-azido-benzoyl)-[(2-methoxycarbonyl-1-(R,S)-phenyl-ethylcarbamoyl)-methyl]-amino}-pentanedioic acid dimethyl ester: MS 597 (M+H)$^+$; prepared as described in Example 6a).

b) 3-(R,S)-{2-[7-acetylamino-3-(S)-(2-methoxycarbonyl-ethyl)-2,5-dioxo-1,2,3,5-tetrahydro-benzo[e][1,4]diazepin-4-yl]-acetylamino}-3-phenyl-propionic acid methyl ester: MS (ISP) 539 (M+H)$^+$; prepared as described in Example 6b).

c) 3-(R,S)-{2-[7-Amino-3-(S)-(2-methoxycarbonyl-ethyl)-2,5-dioxo-1,2,3,5-tetrahydro-benzo[e][1,4]diazepin-4-yl]-acetylamino}-3-phenyl-propionic acid methyl ester: MS 514 (M+NH$_4$)$^+$; prepared as described in Example 6c).

d) 3-(R,S)-{2-[7-amino-3-(S)-(2-carboxy-ethyl)-2,5-dioxo-1,2,3,5-tetrahydro-benzo[e][1,4]diazepin-4-yl]-acetylamino}-3-phenyl-propionic acid: MS (ISN) 467 (M–H)$^-$; prepared as described in Example 6d).

EXAMPLE 10

To a solution of 3-(R,S)-{2-[7-amino-3-(S)-benzyl)2,5-dioxo-1,2,3,5-tetrahydro-benzo[e][1,4]diazepin-4-yl]-acetylamino}-butyric acid (0.6 mmol, 254mg). in DMF (9 ml) was added benzylisocyanate (450 µl 3.2 mmol). The mixture was shaken at 45° C. over night and then evaporated to dryness. The crude product was purified by RP-HPLC to give 3-(R,S)-{2-[3-(S)-benzyl-7-(3-benzyl-ureido)-2,5-dioxo-1,2,3,5-tetrahydro-benzo[e][1,4]diazepin-4-yl]-acetylamino}-butyric acid: MS (ISP) 556 (M–H)$^-$.

The starting material was prepared as follows:

a) 3-(R,S)-(2-{(5-acetylamino-2-azido-benzoyl)-[2-(S)-phenyl-1-methoxycarbonyl-ethyl]-amino}-acetylamino)-butyric acid ethyl ester: MS 570 (M+NH$_4$)$^+$, prepared as described in Example 6a).

b) 3-(R,S)-{2-[7-acetylamino-3-(S)-benzyl-2,5-dioxo-1,2,3,5-tetrahydro-benzo[e][1,4]diazepin-4-yl]-acetylamino}-butyric acid ethyl ester: MS (ISP) 495 (M+H)$^+$ prepared as described in Example 6b).

c) 3-(R,S)-{2-[7-Amino-3-(S)-benzyl-2,5-dioxo-1,2,3,5-tetrahydro-benzo[e][1,4]diazepin-4-yl]-acetylamino}-butyric acid methyl ester: MS 439 (M+H)$^+$; prepared as described in Example 6c).

d) 3-(R,S)-{2-[7-Amino-3-(S)-benzyl-2,5-dioxo-1,2,3,5-tetrahydro-benzo[e][1,4]diazepin-4-yl]-acetylamino}-butyric acid: MS (ISN) 423 (M–H)+; prepared as described in Example 6d).

EXAMPLE 11

To a solution of 3-(R,S)-{2-[7-Amino-3-(S)-(4-hydroxy-benzyl)-2,5-dioxo-1,2,3,5-tetrahydro-benzo[e][1,4]diazepin-4-yl]-acetylamino}-butyric acid (0.2 mmol, 88mg). in DMF (6 ml) was added benzylisocyanate (158 µl 1.2 mmol). The mixture was shaken at 45° C. over night and then was evaporated to dryness. The crude product was purified by RP-HPLC to give 3-(R,S)-{2-[7-(3-benzyl-ureido)-3-(S)-(4-hydroxy-benzyl)-2,5-dioxo-1,2,3,5-tetrahydro-benzo[e][1,4]diazepin-4-yl]-acetylamino}-butyric acid: MS (ISN) 572 (M–H)–.

The starting material was prepared as follows:

a) 3-(R,S)-(2-{(5-acetylamino-2-azido-benzoyl)-[2-(S)-(4-tert-butoxy-phenyl)-1-methoxycarbonyl-ethyl]-amino}-acetylamino)-butyric acid ethyl ester: MS 642 (M+NH$_4$)+; prepared as described in Example 6a).

b) 3-(R,S)-{2-[7-acetylamino-3-(S)-(4-tert-butoxy-benzyl)-2,5-dioxo-1,2,3,5-tetrahydro-benzo[e][1,4]diazepin-4-yl]-acetylamino}-butyric acid ethyl ester: MS 567 (M+H)+; prepared as described in Example 6b).

c) 3-(R,S)-{2-[7-amino-3-(S)-(4-hydroxy-benzyl)-2,5-dioxo-1,2,3,5-tetrahydro-benzo[e][1,4]diazepin-4-yl]-acetylamino}-butyric acid methyl ester: MS 455 (M+H)+; prepared as described in Example 6c).

d) 3-(R,S)-{2-[7-amino-3-(S)-(4-hydroxy-benzyl)-2,5-dioxo-1,2,3,5-tetrahydro-benzo[e][1,4]diazepin-4-yl]-acetylamino}-butyric acid: MS 458 (M+NH$_4$)+; prepared as described in Example 6d).

EXAMPLE 12

To a solution of 3-(R,S)-{2-[7-amino-3-(S)-isopropyl-2,5-dioxo-1,2,3,5-tetrahydro-benzo[e][1,4]diazepin-4-yl]-acetylamino}-butyric acid (0.24 mmol, 90mg). in DMF (8 ml) was added benzylisocyanate (190 µl 1.5 mmol). The mixture was shaken at 45° C. over night and was evaporated to dryness. The crude product was purified by RP-HPLC to give 3-(R,S)-{2-[7-(3-benzyl-ureido)-3-(S)-isopropyl-2,5-dioxo-1,2,3,5-tetrahydro-benzo[e][1,4]diazepin yl]-acetylamino}-butyric acid: MS (ISP) 508 (M–H)–.

The starting material was prepared as follows:

a) 2-(S)-{(5-acetylamino-2-azido-benzoyl)-[(2-ethoxycarbonyl-1-(R,S)-methyl-ethylcarbamoyl)-methyl]-amino}-3-methyl-butyric acid methyl ester; prepared as described in Example 6a).

b) 3-(R,S)-[2-(7-acetylamino-3-(S)-isopropyl-2,5-dioxo-1,2,3,5-tetrahydro-benzo[e][1,4]diazepin-4-yl)-acetylamino]-butyric acid ethyl ester: MS 447 (M+H)+, prepared as described in Example 6b).

c) 3-(R,S)-[2-(7-amino-3-(S)-isopropyl-2,5-dioxo-1,2,3,5-tetrahydro-benzo[e][1,4]diazepin-4-yl)-acetylamino]-butyric acid methyl ester: MS 389 (M–H)–; prepared as described in Example 6c).

d) 3-(R,S)-[2-(7-amino-3-(S)-isopropyl-2,5-dioxo-1,2,3,5-tetrahydro-benzo[e][1,4]diazepin-4-yl)-acetylamino]-butyric acid: MS 394 (M+NH$_4$)+; prepared as described in Example 6d).

EXAMPLE 13

Hydrolysis of (R,S)-3-[2-[6-(3-benzyl-ureido)-1-methyl-2,4-dioxo-1,4-dihydro-2H-quinazolin-3-yl]-acetylamino]-3-phenyl-propionic acid ethyl ester in the presence of K$_2$CO$_3$ in EtOH/H$_2$O as described in Example 2 b) yielded (R,S)-3-[2-[6-(3-benzyl-ureido)-1-methyl-2,4-dioxo-1,4-dihydro-2H-quinazolin-3-yl]-acetylamino]-3-phenyl-propionic acid): mp. 220–222° C.; MS (ISP): 530 (M+1)+.

The starting material can be prepared as follows:

a) Nitration of (1-methyl-2,4-dioxo-1,4-dihydro-2H-quinazolin-3-yl)-acetic acid (M. Süsse et al., Monatsh Chem 1987, 118, 71–79) as described in Example 1b) produced (1-methyl-6-nitro-2,4-dioxo-1,4-dihydro-2H-quinazolin-3-yl)-acetic acid: mp. 217–220° C.; MS (EI): 279 (M)+.

b) Coupling of (1-methyl-6-nitro-2,4-dioxo-1,4-dihydro-2H-quinazolin-3-yl)-acetic acid with (R,S)-3-amino-3-phenyl-propanoic acid ethyl ester in the presence of EEDQ as described in Example 2 c) yielded (R,S)-3-[2-(1-methyl-6-nitro-2,4-dioxo-1,4-dihydro-2H-quinazolin-3-yl)-acetylamino]-3-phenyl-propionic acid ethyl ester: mp. 160–162° C.; MS (ISP): 455 (M+1)+.

c) Catalytic hydrogenation of (R,S)-3-[2-(1-methyl-6-nitro-2,4-dioxo-1,4-dihydro-2H-quinazolin 3-yl)-acetylamino]-3-phenyl-propionic acid ethyl ester as described in Example 3 c) gave (R,S)-3-[2-(6-amino-1-methyl-2,4-dioxo-1,4-dihydro-2H-quinazolin-3-yl)-acetylamino]-3-phenyl-propionic acid ethyl ester: mp. 155–160° C.; MS (ISP): 425 (M+1)+.

d) Reaction of (R,S)-3-[2-(6-amino-1-methyl-2,4-dioxo-1,4-dihydro-2H-quinazolin-3-yl)-acetylamino]-3-phenyl-propionic acid ethyl ester with benzylisocyanate as described in Example 1 d) yielded (R,S)-3-[2-[6-(3-benzyl-ureido)-1-methyl-2,4-dioxo-1,4-dihydro-2H-quinazolin-3-yl]-acetylamino]-3-phenyl-propionic acid ethyl ester: mp. 217–219° C.; MS (ISP): 558 (M+1)+.

EXAMPLE 14

Treatment of (R,S)-3-[2-(6-(N$^2$, N$^3$-bis(tert-butoxycarbonyl)guanidino-1-methyl-2,4-dioxo-1,4-dihydro-2H-quinazolin-3-yl)-acetylamino]-3-phenyl-propionic acid ethyl ester with TFA followed by LiOH as described in Example 2 yielded (R,S)-3-[2-(6-guanidino-1-methyl-2,4-dioxo-1,4-dihydro-2H-quinazolin-3-yl)-acetylamino]-3-phenyl-propionic acid: mp. 306–308° C. (dec); MS (ISP): 439 (M+1)+.

The starting material was prepared as follows:

Reaction of (R,S)-3-[2-(6-amino-1-methyl-2,4-dioxo-1,4-dihydro-2H-quinazolin-3-yl)-acetylamino]-3-phenyl-propionic acid ethyl ester (Example 13 c)) with N, N$^2$-bis(tert-butoxycarbonyl)-S-methylisothiourea in the presence of Hg(OAc)$_2$ as described in Example 2 a) led to (R,S)-3-[2-(6-(N$^2$, N$^3$-bis(tert-butoxycarbonyl)guanidino-1-methyl-2,4-dioxo-1,4-dihydro-2H-quinazolin-3-yl)-acetylamino]-3-phenyl-propionic acid ethyl ester in form of a colorless resin: MS (ISP): 667 (M+1)+.

EXAMPLE 15

Hydrolysis of 3-{2-[7-(3-benzyl-ureido)-5-oxo-2,3-dihydro-5H-benzo[f][1,4]oxazepin-4-yl]-acetylamino}-propionic acid ethyl ester with aqueous LiOH as described in Example 1 yielded 3-{2-[7-(3-benzyl-ureido)-5-oxo-2,3-dihydro-5H-benzo[f][1,4]oxazepin-4-yl]-acetylamino}-propionic acid in form of a tan foam: MS (ISP): 441 (M+1)+.

The starting material was prepared as follows:

a) Coupling of 2-fluoro-5-nitro-benzoic acid (Aldrich) with (2-hydroxy-ethylamino)-acetic acid tert-butyl ester (G. Breipohl et al., Tetrahedron 1997, 53, 14671) in dichloromethane in the presence of DCC gave, after usual work-up and purification by chromatography on silica gel

[(2-fluoro-5-nitro-benzoyl)-(2-hydroxy-ethyl)-amino]-acetic acid tert-butyl ester as a pale yellow resin: MS (ISP): 287 (M–56)$^+$.

b) Treatment of [(2-fluoro-5-nitro-benzoyl)-(2-hydroxy-ethyl)-amino]-acetic acid tert-butyl ester (3.08 g, 9 mmol) in dichloromethane (25 ml) with DBU (2.5 ml) at 35° C. for 24 h gave after evaporation of the solvents and purification (silica gel, dichloromethane/MeOH 19:1) (7-nitro-5-oxo-2,3-dihydro-5H-benzo[f][1,4]oxazepin-4-yl)-acetic acid tert-butyl ester (2.3 g, 7.1 mmol): mp. 116–118° C.; MS (EI): 322 (M)$^+$.

c) Treatment of (7-nitro-5-oxo-2,3-dihydro-5H-benzo[f][1,4]oxazepin-4-yl)-acetic acid tert-butyl ester (2.3 g, 7.1 mmol) with TFA (2 ml) in dichloromethane (20 ml) at 35° C. for 5 h gave, after evaporation of the solvents, trituration with ethyl acetate, filtration and washing, (7-nitro-5-oxo-2,3-dihydro-5H-benzo[f][1,4]oxazepin-4-yl)-acetic acid (1.55 g, 5.8 mmol): mp. 190° C.; MS (EI): 266 (M)$^+$.

d) Coupling of (7-nitro-5-oxo-2,3-dihydro-5H-benzo[f][1,4]oxazepin-4-yl)-acetic acid (0.53 g, 2 mmol) with the hydrochloride salt of beta-alanine ethyl ester in dichloromethane in the presence of HBTU and NEt$_3$ gave after usual work-up and purification by chromatography (SiO$_2$, dichloromethane/MeOH 29:1) 3-[2-(7-nitro-5-oxo-2,3-dihydro-5H-benzo[f][1,4]oxazepin-4-yl)-acetylamino]-propionic acid ethyl ester (0.68 g, 1.86 mmol): mp. 110–120° C.; MS (ISP): 366 (M+1)$^+$.

e) Hydrogenation of 3-[2-(7-nitro-5-oxo-2,3-dihydro-5H-benzo[f][1,4]oxazepin-4-yl)-acetylamino]-propionic acid ethyl ester (0.65 g, 1.78 mmol) as described in Example 3 c) gave 3-[2-(7-amino-5-oxo-2,3-dihydro-5H-benzo[f][1,4]oxazepin-4-yl)-acetylamino]-propionic acid ethyl ester (0.42 g, 1.25 mmol) as waxy solid: MS (ISP): 336 (M+1)$^+$.

f) Treatment of 3-[2-(7-amino-5-oxo-2,3-dihydro-5H-benzo[f][1,4]oxazepin-4-yl)-acetylamino]-propionic acid ethyl ester (0.17 g, 0.5 mmol) with benzylisocyanate as described in Example 1 d) yielded 3-{2-[7-(3-benzyl-ureido)-5-oxo-2,3-dihydro-5H-benzo[f][1,4]oxazepin-4-yl]-acetylamino}-propionic acid ethyl ester (0.2 g, 0.42 mmol): mp. 70–75° C.; MS (ISP): 469 (M+1)$^+$.

EXAMPLE 16

Hydrolysis of (R,S)-3-[2-[7-(3-benzyl-ureido)-5-oxo-2,3-dihydro-5H-benzo[f][1,4]oxazepin-4-yl]-acetylamino]-3-phenyl-propionic acid ethyl ester with aqueous LiOH as described in Example 1 yielded (R,S)-3-[2-[7-(3-benzyl-ureido)-5-oxo-2,3-dihydro-5H-benzo[f][1,4]oxazepin-4-yl]-acetylamino]-3-phenyl-propionic acid: mp. 285° C.; MS (ISP): 517 (M+1)$^+$.

The starting material was prepared as follows:

a) Coupling of (7-nitro-5-oxo-2,3-dihydro-5H-benzo[f][1,4]oxazepin-4-yl)-acetic acid (0.53 g, 2 mmol, Example 15 c) with the hydrochloride salt of (R,S)-3-amino-3-phenyl-propanoic acid ethyl ester in dichloromethane in the presence of HBTU and NEt$_3$ gave, after usual work-up and purification by chromatography (SiO$_2$, dichloromethane/MeOH 19:1), (R,S)-3-[2-(7-nitro-5-oxo-2,3-dihydro-5H-benzo[f][1,4]oxazepin-4-yl)-acetylamino]-3-phenyl-propionic acid ethyl ester (0.52 g, 1.18 mmol) in form of a pale yellow resin: MS (ISP): 442 (M+1)$^+$.

b) Catalytic hydrogenation of (R,S)-3-[2-(7-nitro-5-oxo-2,3-dihydro-5H-benzo[f][1,4]oxazepin-4-yl)-acetylamino]-3-phenyl-propionic acid ethyl ester followed by treatment of the resulting amine with benzylisocyanate, as described in Example 15 e) and 15 f), furnished (R,S)-3-[2-[7-(3-benzyl-ureido)-5-oxo-2,3-dihydro-5H-benzo[f][1,4]oxazepin-4-yl]-acetylamino]-3-phenyl-propionic acid ethyl ester: mp. 95–100° C.; MS (ISP): 545 (M+1)$^+$.

EXAMPLE 17

Hydrolysis of (R,S)-3-{2-[7-(3-benzyl-3-methyl-ureido)-5-oxo-2,3-dihydro-5H-benzo[f][1,4]oxazepin-4-yl]-acetylamino}-3-pyridin-3-yl-propionic acid ethyl ester with aqueous LiOH as described in Example 1 yielded the hydrochloride salt of (R,S)-3-{2-[7-(3-benzyl-3-methyl-ureido)-5-oxo-2,3-dihydro-5H-benzo[f][1,4]oxazepin-4-yl]-acetylamino}-3-pyridin-3-yl-propionic acid: mp. 140–140° C. (dec.); MS (ISP): 518 (M+1)$^+$.

The starting material was prepared as follows:

a) Catalytic hydrogenation of (7-nitro-5-oxo-2,3-dihydro-5H-benzo[f][1,4]oxazepin-4-yl)-acetic acid (Example 15 c) followed by treatment of the resulting amine with benzylisocyanate yielded [7-(3-benzyl-ureido)-5-oxo-2,3-dihydro-5H-benzo[f][1,4]oxazepin-4-yl]-acetic acid: mp. 60–70° C. (dec.); MS (ISP): 370 (M+1)$^+$.

b) Coupling of [7-(3-benzyl-ureido)-5-oxo-2,3-dihydro-5H-benzo[f][1,4]oxazepin-4-yl]-acetic acid with the hydrochloride salt of (R,S)-3-pyridin-3-yl-propionic acid ethyl ester in dichloromethane in the presence of HBTU and NEt$_3$ gave, after usual work-up and purification by chromatography (SiO$_2$, dichloromethane/MeOH 29:1), (R,S)-3-{2-[7-(3-benzyl-3-methyl-ureido)-5-oxo-2,3-dihydro-5H-benzo[f][1,4]oxazepin-4-yl]-acetylamino}-3-pyridin-3-yl-propionic acid ethyl ester in form of a colorless resin: MS (ISP): 546 (M+1)$^+$.

EXAMPLE 18

Treatment of (S)-2-[2-[2-(7-amino-5-oxo-2,3-dihydro-5H-benzo[f][1,4]oxazepin-4-yl)-acetylamino]-3-carboxy-propionylamino]-benzoic acid with benzylisocyanate as described in Example 1 d), gave (S)-2-[2-[2-[7-(3-benzyl-ureido)-5-oxo-2,3-dihydro-5-H-benzo[f][1,4]oxazepin-4-yl]-acetylamino]-3-carboxy-propionylamino]-benzoic acid as acetate salt: mp. 166° C. (dec.); MS (ISP): 604 (M+1)$^+$.

The starting material was prepared as follows:

a) Coupling of (7-nitro-5-oxo-2,3-dihydro-5H-benzo[f][1,4]oxazepin-4-yl)-acetic acid (Example 15 c) with 2-[2-amino-3-benzyloxycarbonyl)-propionylamino]-benzoic acid benzyl ester (prepared by coupling of Boc-Asp(OBzl)-OH with benzyl anthranilate followed by treatment with TFA) in dichloromethane in the presence of HBTU and NEt$_3$ gave (S)-2-[3-benzyloxycarbonyl-2-[2-(7-nitro-5-oxo-2,3-dihydro-5H-benzo[f][1,4]oxazepin-4-yl)-acetylamino]-propionylamino]-benzoic acid benzyl ester: mp. 64–65° C. (dec.); MS (ISP): 681 (M+1)$^+$.

b) Catalytic hydrogenation of (S)-2-[3-benzyloxycarbonyl-2-[2-(7-nitro-5-oxo-2,3-dihydro-5H-benzo[f][1,4]oxazepin-4-yl)-acetylamino]-propionylamino]-benzoic acid benzyl ester in EtOH in the presence of 10% Pd—C gave (S)-2-[2-[2-(7-amino-5-oxo-2,3-dihydro-5H-benzo[f][1,4]oxazepin-4-yl) -acetylamino]-3-carboxy-propionylamino]-benzoic acid as an amorphous powder: MS (ISP): 471 (M+1)$^+$.

EXAMPLE 19

Hydrolysis of (R,S)-3-{2-[7-(3-butyl-ureido)-5-oxo-2,3-dihydro-5H-benzo[f][1,4]oxazepin-4-yl]-acetylamino}-3-pyridin-3-yl-propionic acid ethyl ester in the presence of aqueous LiOH as described in Example 1 produced, after purification of the crude material by chromatography (silica gel RP-18, water-MeOH gradient) (R,S)-3-{2-[7-(3-butyl-ureido)-5-oxo-2,3-dihydro-5H-benzo[f][1,4]oxazepin-4-yl]-acetylamino}-3-pyridin-3-yl-propionic acid mp. 140° C. (dec.); MS (ISP): 484 (M+1)$^+$.

The starting material was prepared as follows:
a) Coupling of (7-nitro-5-oxo-2,3-dihydro-5H-benzo[f][1,4]oxazepin-4-yl)-acetic acid (1.33 g, 5 mmol, Example 15 c) with the hydrochloride salt of (R,S)-3-amino-3-pyridin-3-yl-propanoic acid ethyl ester in dichloromethane in the presence of HBTU and NEt$_3$ gave, after usual work-up and purification by chromatography (SiO$_2$, dichloromethane/MeOH 19:1), (R, S)-3-[2-(7-nitro-5-oxo-2,3-dihydro-5H-benzo[f [1,4]oxazepin-4-yl)-acetylamino]-3-pyridin-3-yl-propionic acid ethyl ester (1.7 g, 3.84 mmol) in form of a pale yellow resin: MS (ISP): 443 (M+1)$^+$.
b) Catalytic hydrogenation of (R,S)-3-[2-(7-nitro-5-oxo-2,3-dihydro-5H-benzo[f][1,4]oxazepin-4-yl)-acetylamino]-3-pyridin-3-yl-propionic acid ethyl ester followed by treatment of the resulting amine with n-butylisocyanate as described in Examples 3c) and 1d) yielded, after usual work-up and purification by chromatography (silica gel, dichloromethane/MeOH 19:1), (R,S)-3-{2-[7-(3-butyl-ureido)-5-oxo-2,3-dihydro-5H-benzo[f][1,4]oxazepin-4-yl]-acetylamino}-3-pyridin-3-yl-propionic acid ethyl ester as colorless foam: MS (ISP): 512 (M+1)$^+$.

EXAMPLE 20

Hydrolysis of (R,S)-3-(2-{7-[3-(4-fluoro-benzyl)-ureido]-5-oxo-2,3-dihydro-5H-benzo[f][1,4]oxazepin-4-yl}-acetylamino)-3-pyridin-3-yl-propionic acid ethyl ester in the presence of aqueous LiOH as described in Example 1 gave, after purification of the crude material by chromatography (silica gel RP-18, water/MeOH gradient), (R,S)-3-(2-{7-[3-(4-fluoro-benzyl)-ureido]-5-oxo-2,3-dihydro-5H-benzo[f][1,4]oxazepin-4-yl}-acetylamino)-3-pyridin-3-yl-propionic acid: mp. 150–160° C. (dec.); MS (ISN): 534 (M−1)$^+$.

The starting material was prepared as follows:
Catalytic hydrogenation of (R,S)-3-[2-(7-nitro-5-oxo-2,3-dihydro-5H-benzo[f][1,4]oxazepin-4-yl)-acetylamino]-3-pyridin-3-yl-propionic acid ethyl ester (Example 19 a) followed by treatment of the resulting amine with 4-fluoro-benzylisocyanate as described in Examples 3c) and 1d) yielded, after usual work-up and purification by chromatography (silica gel, dichloromethane/MeOH 19:1), (R,S)-3-(2-{7-[3-(4-fluoro-benzyl)-ureido]-5-oxo-2,3-dihydro-5H-benzo[f][1,4]oxazepin-4-yl}-acetylamino)-3-pyridin-3-yl-propionic acid ethyl ester: mp. 90–95° C.; MS (ISP) 564 (M+1)$^+$.

EXAMPLE 21

Hydrolysis of (R,S)-3-{2-[7-(3-benzyl-ureido)-5-oxo-2-phenyl-2,3-dihydro-5H-benzo[f][1,4]oxazepin-4-yl]-acetylamino}-3-phenyl-propionic acid ethyl ester (0.15 g, 0.24 mmol) in the presence of aqueous LiOH, as described in Example 1, yielded (R,S)-3-{2-[7-(3-benzyl-ureido)-5-oxo-2-phenyl-2,3-dihydro-5H-benzo[f][1,4]oxazepin-4-yl]-acetylamino}-3-phenyl-propionic acid (0.125 g, 0.21 mmol): mp. 138–140° C.; MS (ISP) 593 (M+1)$^+$.

The starting material was prepared as follows:
a) Coupling of 2-fluoro-5-nitro-benzoic acid (Aldrich) with (R,S)-(2-hydroxy-2-phenyl-ethylamino)-acetic acid tert-butyl ester (prepared by monoalkylation of (R,S)-2-amino-2-phenyl-ethanol using t-butyl bromoacetate in the presence of NEt$_3$ according to the procedure by G. Breipohl et al., Tetrahedron 1997, 53, 14671; see also H. Kotsuki et al., Chem Lett 1994, 11, 2159) in dichloromethane in the presence of HBTU and NMM gave, after usual work-up and purification by chromatography (silica gel, dichloromethane/MeOH 19:1), (R,S)-[(2-fluoro-5-nitro-benzoyl)-(2-hydroxy-2-phenyl-ethyl)-amino]-acetic acid tert-butyl ester as a pale yellow resin: MS (EI) 419 (M+1)$^+$.
b) Treatment of (R,S)-[(2-fluoro-5-nitro-benzoyl)-(2-hydroxy-2-phenyl-ethyl)-amino]-acetic acid tert-butyl ester (1.4 g, 3.35 mmol) in THF (25 ml) with DBU (1 ml) at RT for 20 h gave after evaporation of the solvents and purification (silica gel, dichloromethane) (R,S)-(7-nitro-5-oxo-2-phenyl-2,3-dihydro-5H-benzo[f][1,4]oxazepin-4-yl)-acetic acid tert-butyl ester (0.6 g, 1.5 mmol): mp. 150–151° C.; MS (EI): 398 (M)$^+$.
c) Treatment of (R,S)-(7-nitro-5-oxo-2-phenyl-2,3-dihydro-5H-benzo[f][1,4]oxazepin-4-yl)-acetic acid tert-butyl ester with TFA followed by coupling of the resulting acid with (R,S)-3-amino-3-phenyl-propanoic acid ethyl ester, as described in Example 15 c) and d), gave after purification by chromatography ( silica gel, dichloromethane/MeOH 19:1) (R,S)-3-[2-(7-nitro-5-oxo-2-phenyl-2,3-dihydro-5H-benzo[f][1,4]oxazepin-4-yl)-acetylamino]-3-phenyl-propionic acid ethyl ester as colourless foam: MS (ISP): 518 (M)$^+$.
d) Reduction of (R,S)-3-[2-(7-nitro-5-oxo-2-phenyl-2,3-dihydro-5H-benzo[f][1,4]oxazepin-4-yl)-acetylamino]-3-phenyl-propionic acid ethyl ester with SnCl$_2$.2 H$_2$O in EtOH followed by treatment of the resulting amine with benzylisocyanate yielded, after purification by chromatography (silica gel, dichloromethane/MeOH 29:1), (R,S)-3-{2-[7-(3-benzyl-ureido)-5-oxo-2-phenyl-2,3-dihydro-5H-benzo[f][1,4]oxazepin-4-yl]-acetylamino}-3-phenyl-propionic acid ethyl ester: mp. 95–100° C.; MS (ISP): 621 (M+1)$^+$.

EXAMPLE 22

80 mg (0.22 mmol) 6-(7-acetylamino-2,5-dioxo-1,2,3,5-tetrahydro-benzo[e][1,4]diazepin-4-yl)-hexanoic acid methyl ester was dissolved in 1 ml MeOH/HCl (freshly prepared from 10 ml MeOH and 1 ml SOCl$_2$). The solution was stirred for 18 h and concentrated in vacuo. The residue was taken up in 2 ml of THF/MeOH (1: 1) and 0.5 ml 1N aqueous NaOH was added. After stirring for 16 h at 22° C. the mixture was neutralised by addition of solid carbon dioxide, and the solvents were evaporated. The residue was taken up in DMF (2.5 ml) and 0.032 ml benzylisocyanate (0.26 mmol) was added. The mixture was shaken at 45° C. over night and evaporated. The crude product was purified by preparative HPLC to give 6-[7-(3-benzyl-ureido) -2,5-dioxo-1,2,3,5-tetrahydro-benzo[e][1,4]diazepin-4-yl]-hexanoic acid (19 mg, 0.043 mmol): MS (ISN) 437(M−H)$^−$.

The starting material was prepared as follows:
a) 500 mg polymerbound triphenylphosphine (Fluka #93093) was added to 267 mg (0.55 mmol) 6-{(5-acetylamino-2-azido-benzoyl)-cyclohexylcarbamoyl-methyl-amino}-hexanoic acid methyl ester in 8 ml 1,2-dichloroethane. The suspension was heated to 50° C. for 120 min and the solvent was filtered off. The solid was collected, suspended in a solution consisting of 8 ml AcOH, 1 ml water, and 1 ml dioxane and the mixture was heated to reflux for 24 h and filtered. The filtrate was concentrated in vacuo and the residue flashchromatographed on silicagel in EtOAc/hexane as eluent to yield 6-(7-acetylamino-2,5-dioxo-1,2,3,5-tetrahydro-benzo[e][1,4]diazepin-4-yl)-hexanoic acid methyl ester (117 mg, 0.32 mmol): MS (ISP) 362(M+H)$^+$.

b) Cyclohexylisocyanide(0.73 ml) was added to a slurry consisting of 1.09 g (6.0 mmol) 6-aminohexanoic acid methylester HCl, 1.03 ml (6.0 mmol) DIPEA, 0.46 ml formaldehyde (36.5% in $H_2O$), and 1.32 g (6.0 mmol) 5-acetamido-2-azido-benzoic acid in 15 ml MeOH. The reaction mixture was stirred for 18 h, filtered, and the filtrate evaporated. The brown residue was purified by flash chromatography on silica gel in EtOAc/hexane to give 2.19 g (75%) colourless crystals of 6-[(5-acetylamino-2-azido-benzoyl)-cyclohexylcarbamoyl-methylamino]-hexanoic acid ethyl ester: MS 504 $(M+NH_4)^+$.

EXAMPLE 23

In analogy to the procedure in Example 22 starting with (R,S)-6-[7-acetylamino-2,5-dioxo-1,2,3,5-tetrahydro-benzo[e][1,4]diazepin-4-yl]-3-phenyl-hexanoic acid ethyl ester (90 mg, 0.20 mmol) yielded (R,S)-6-[7-(3-benzyl-ureido)-2,5-dioxo-1,2,3,5-tetrahydro-benzo[e][1,4]diazepin-4-yl]-3-phenyl-hexanoic acid (28 mg, yield 31%): MS (ISN) 513 (M−H).

The starting material was prepared as follows:
a) Following the procedure in Example 22 starting with 256 mg (R,S)-6-[(5-acetylamino-2-azido-benzoyl)-cyclohexylcarbamoylmethyl-amino]-3-phenyl-hexanoic acid ethyl ester there was obtained 135 mg (R,S)-6-[7-acetylamino-2,5-dioxo-1,2,3,5-tetrahydro-benzo[e][1,4]diazepin-4-yl]-3-phenyl-hexanoic acid ethyl ester. MS (ISP) 452$(M+H)^+$.
b) Following the procedure in Example 22 starting with 0.73 ml cyclohexylisocyanide, 1.63 g (6.0 mmol) (R,S)-6-amino-3-phenylhexanoic acid ethyl ester HCl, 1.03ml (6.0 mmol) DIPEA, 0.46 ml formaldehyde (36.5% in $H_2O$), and 1.32 g (6.0 mmol) 5-acetamido-2-azido-benzoic acid in 15 ml MeOH there was obtained 2.38 g (R,S)-6-[(5-acetylamino-2-azido-benzoyl)-cyclohexylcarbamoylmethyl-amino]-3-phenyl-hexanoic acid ethyl ester: MS 594 $(M+NH_4)^+$.

EXAMPLE A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

| | |
| --- | --- |
| AcOH | acetic acid |
| Aeg-RGDS | aminoethylglycine-Arg-Gly-Asp-Ser-OH |
| Boc | tert-butoxycarbonyl |
| BOP | (benzotriazol-1-yloxy)-tris-(dimethylamino)-phosphonium-hexa-fluorophosphate |
| BSA | bovine serum albumin |
| Cbz | benzyloxycarbonyl |
| CDMT | 2-chloro-4,6-dimethoxy-1,3,5-triazine |
| DBU | 1,8-diazabicyclo[5.4.0]undec-7-ene |
| DCC | 1,3-dicyclohexylcarbodiimide |
| DIPEA | N,N-diisopropylethylamine |
| DMAP | 4-dimethylaminopyridine |
| DMF | N,N-dimethylformamide |
| EDC | N-(3-dimethylaminopropyl)-N'-ethyl-carbodiimide-hydrochloride |
| EEDQ | (2-ethoxy-1-ethoxycarbonyl)-1,2-dihydroquinoline |
| EI | electron impact |
| ELISA | enzyme-linked immunosorbent assay |
| EtOH | ethanol |
| FAB | fast atom bombardment |
| HBTU | O-(benzotriazol-1-yl)-N,N,N',N'-tetramethyluronium-hexafluoro-phosphate |
| ISP | ion spray (positively charged ions) |
| ISN | ion spray (negatively charged ions) |
| MeCN | acetonitrile |
| MeOH | methanol |
| MS | mass spectroscopy |
| NMM | N-methylmorpholine |
| RGDS | H-Arg-Gly-Asp-Ser-OH |
| RP | reversed phase |
| RT | room temperature |
| mp | melting point |
| t-BuOH | tert-butanol |
| TFA | trifluoro acetic acid |
| THF | tetrahydrofuran |

What is claimed is:
1. A compound of formula I

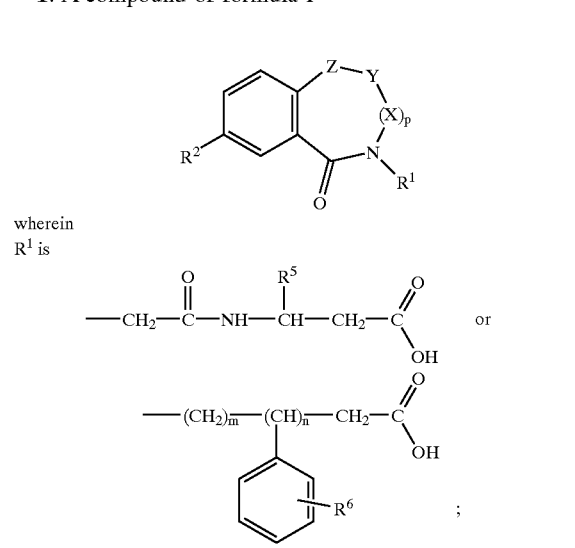

wherein
$R^1$ is $R^2$ is

-continued

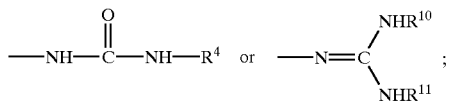

R³ is hydrogen, alkyl, C₃₋₈ monocyclic, aralkyl, aryl or carboxyalkyl;
R⁴ is alkyl or aralkyl;
R,⁵ is hydrogen, alkyl, aryl, saturated, partially unsaturated or aromatic 5- to 10-membered heterocycle that contains one or more hetero atoms selected from nitrogen, oxygen and sulfur, or R⁵ is —CO—NH—R⁸;
R⁶ is hydrogen or

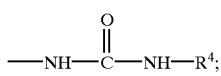

R⁷ is hydrogen, alkyl, C₃₋₈ monocyclic or aralkyl;
R⁸ is alkyl, C₃₋₈ monocyclic, aralkyl or aryl;
R⁹ is hydrogen, alkyl, C₃₋₈ monocyclic, aryl or aralkyl;
R¹⁰ and R¹¹ are each independently hydrogen or alkyl or R¹⁰ and R¹¹ together with the N-atoms to which they are attached form an imidazolidin or hexahydropyrimidine ring that is unsubstituted or is alkyl-substituted;
X is —CH(R³)—;
Z is —N(R⁷)— or oxygen, wherein Y is —CO— when Z is —N(R⁷)— and Y is —CH(R⁹)— when Z is oxygen;
m, n and p are zero or whole positive numbers, wherein m is 2 to 5; n is zero or 1; p is zero or 1;
or a pharmaceutically usable salt thereof or a pharmaceutically usable ester thereof that is formed by esterifying one or more of the —COOH groups in substituents R¹ and R³.

2. The compound according to claim 1, wherein R³ is hydrogen, alkyl, aralkyl or carboxyalkyl.
3. The compound according to claim 1, wherein R⁵ is hydrogen, methyl, phenyl, pyridyl or —CO—NH—R⁸.
4. The compound according to claim 1, wherein R⁷ is hydrogen or alkyl.
5. The compound according to claim 1, wherein R⁸ is aryl.
6. The compound according to claim 1, wherein R⁹ is hydrogen or aryl.
7. The compound according to claim 1, wherein R¹⁰ and R¹¹ are hydrogen.
8. The compound according to claim 1, wherein p is 1 and Z is oxygen.
9. The compound according to claim 1, wherein m is 3 to 4.
10. The compound according to claim 1, wherein p is 1.
11. The compound according to claim 1 of the formula

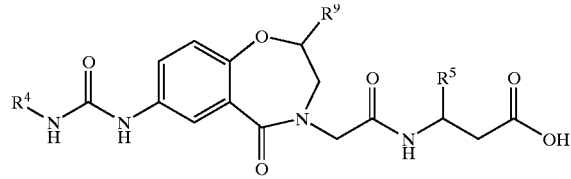

wherein
R⁴ is alkyl, unsubstituted benzyl or halo-substituted benzyl;

R⁵ is hydrogen, unsubstituted phenyl, pyridyl or

R⁸ is carboxy-substituted phenyl; and
R⁹ is hydrogen or unsubstituted phenyl.
12. The compound

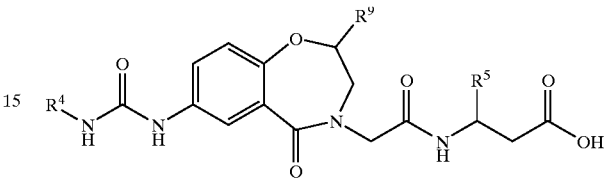

wherein
R⁴ is alkyl, unsubstituted benzyl or benzyl substituted with fluorine, chlorine or bromine;
R⁵ is hydrogen, unsubstituted phenyl, pyridyl or

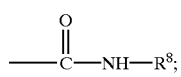

R⁸ is carboxy-substituted phenyl; and
R⁹ is hydrogen or unsubstituted phenyl.
13. The compound according to claim 12, wherein R⁵ is hydrogen and R⁹ is hydrogen.
14. The compound according to claim 13, wherein the compound is 3-{2-[7-(3-benzyl-ureido)-5-oxo-2,3-dihydro-5H-benzo[f][1,4]oxazepin-4-yl]-acetylamino}-propionic acid.
15. The compound according to claim 12, wherein R⁵ is unsubstituted phenyl.
16. The compound according to claim 15, wherein the compound is (R,S)-3-[2-[7-(3-benzyl-ureido)-5-oxo-2,3-dihydro-5H-benzo[f][1,4]oxazepin-4-yl]-acetylamino]-3-phenyl-propionic acid.
17. The compound according to claim 15, wherein the compound is (R,S)-3-{2-[7-(3-benzyl-ureido)-5-oxo-2-phenyl-2,3-dihydro-5H-benzo[f][1,4]oxazepin-4-yl]-acetylamino}-3-phenyl-propionic acid.
18. The compound according to claim 12, wherein R⁵ is 3-pyridyl.
19. The compound according to claim 18, wherein the compound is (R,S)-3-{2-[7-(3-benzyl-3-methyl-ureido)-5-oxo-2,3-dihydro-5H-benzo[f][1,4]oxazepin-4-yl]-acetylamino}-3-pyridin-3-yl-propionic acid.
20. The compound according to claim 18, wherein the compound is (R,S)-3-{2-[7-(3-butyl-ureido)-5-oxo-2,3-dihydro-5H-benzo[f][1,4]oxazepin-4-yl]-acetylamino}-3-pyridin-3-yl-propionic acid.
21. The compound according to claim 18, wherein the compound is (R,S)-3-(2-{7-[3-(4-fluoro-benzyl)-ureido]-5-oxo-2,3-dihydro-5H-benzo[f][1,4]oxazepin-4-yl}-acetylamino)-3-pyridin-3-yl-propionic acid.
22. The compound according to claim 12, wherein $R^5$ is

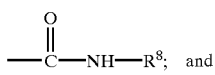

$R^8$ is carboxy-substituted phenyl.

23. The compound according to claim 22, wherein the compound is (S)-2-[2-[2-[7-(3-benzyl-ureido)-5-oxo-2,3-dihydro-5H-benzo[f][1,4]oxazepin-4-yl]-acetylamino]-3-carboxy-propionylamino]-benzoic acid.

24. A process for preparing a compound of formula I

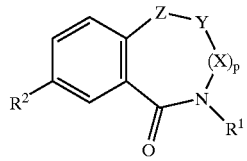

wherein $R^1$ is

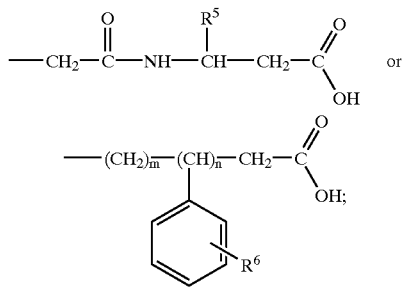

$R^2$ is

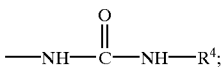

$R^3$ is hydrogen, alkyl, $C_{3-8}$ monocyclic, aralkyl, aryl or carboxyalkyl;

$R^4$ is alkyl or aralkyl;

$R^5$ is hydrogen, alkyl, aryl, saturated, partially unsaturated or aromatic 5- to 10-membered heterocycle that contains one or more hetero atoms selected from nitrogen, oxygen and sulfur, or $R^5$ is —CO—NH—$R^8$;

$R^6$ is hydrogen or

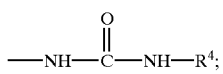

$R^7$ is hydrogen, alkyl, $C_{3-8}$ monocyclic or aralkyl;

$R^8$ is alkyl, $C_{3-8}$ monocyclic, aralkyl or aryl;

$R^9$ is hydrogen, alkyl, $C_{3-8}$ monocyclic, aryl or aralkyl;

X is —CH($R^3$)—;

Z is —N($R^7$)— or oxygen, wherein Y is —CO— when Z is —N($R^7$)— and Y is —CH($R^9$)— when Z is oxygen; and m, n and p are zero or whole positive numbers, wherein m is 2 to 5; n is zero or 1; p is zero or 1;

comprising reacting a compound of formula XXXXV

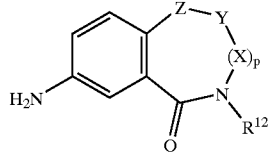

with an isocyanate of the formula $R^4$—N=C=O, wherein $R^{12}$ is

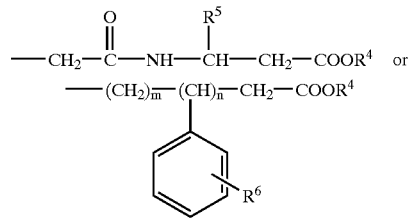

and $R^2$ to $R^{11}$, X, Y, Z, m, n and p are as above, to yield the corresponding compound of formula XXXXVII

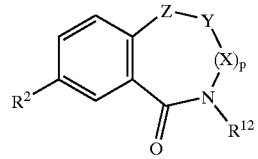

and hydrolyzing the ester groups on $R^{12}$ of the compound of formula XXXXVII to yield the corresponding compound of formula I.

25. A process for preparing a compound of formula I

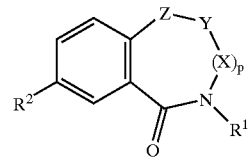

wherein $R^1$ is

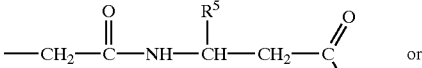

$R^2$ is

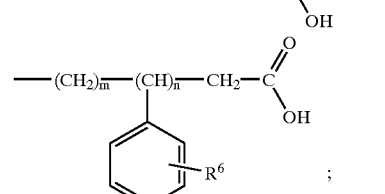

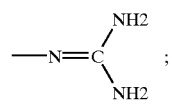

$R^3$ is hydrogen, alkyl, $C_{3-8}$ monocyclic, aralkyl, aryl or carboxyalkyl;

$R^4$ is alkyl or aralkyl;

$R^5$ is hydrogen, alkyl, aryl, saturated, partially unsaturated or aromatic 5- to 10-membered heterocycle that contains one or more hetero atoms selected from nitrogen, oxygen and sulfur, or $R^5$ is —CO—NH—$R^8$;

$R^6$ is hydrogen or

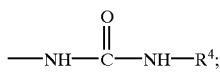

$R^7$ is hydrogen, alkyl, $C_{3-8}$ monocyclic or aralkyl;

$R^8$ is alkyl, $C_{3-8}$ monocyclic, aralkyl or aryl;

$R^9$ is hydrogen, alkyl, $C_{3-8}$ monocyclic, aryl or aralkyl;

$R^{10}$ and $R^{11}$ are each independently hydrogen or alkyl or $R^{10}$ and $R^{11}$ together with the N-atoms to which they are attached form an imidazolidin or hexahydropyrimidine ring that is unsubstituted or is alkyl-substituted;

X is —CH($R^3$)—;

Z is —N($R^7$)— or oxygen, wherein Y is —CO— when Z is —N($R^7$)— and Y is —CH($R^9$)— when Z is oxygen;

m, n and p are zero or whole positive numbers, wherein m is 2 to 5; n is zero or 1; p is zero or 1;

comprising reacting a compound of the formula XXXXV

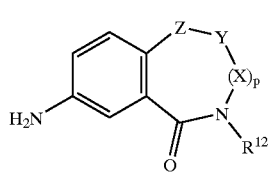

with a guanylation agent in the presence of Hg(OA)$_2$ or HgCl$_2$, wherein $R^{12}$ is

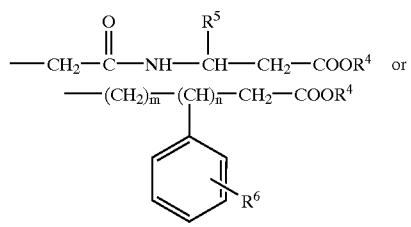

$R^4$ is alkyl or aralkyl; and $R^3$ and $R^5$ to $R^{11}$, X, Y, Z, m, n and p are as above, to yield the corresponding compound of formula XXXXVII

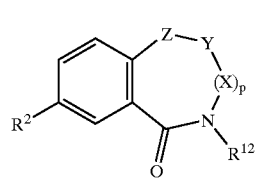

and hydrolyzing the ester groups on $R^{12}$ of the compound of formula XXXXVII to yield the corresponding compound of formula I.

26. A process for preparing a compound of formula I,

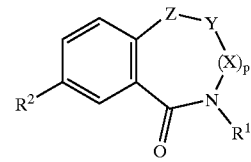

I wherein $R^1$ is

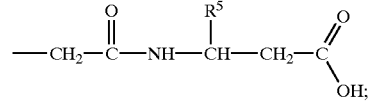

$R^2$ is

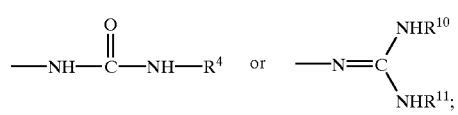

$R^3$ is hydrogen, alkyl, $C_{3-8}$ monocyclic, aralkyl, aryl or carboxyalkyl;

$R^4$ is alkyl or aralkyl;

$R^5$ is hydrogen, alkyl, aryl, saturated, partially unsaturated or aromatic 5- to 10-membered heterocycle that contains one or more hetero atoms selected from nitrogen, oxygen and sulfur, or $R^5$ is —CO—NH—$R^8$;

$R^7$ is hydrogen, alkyl, $C_{3-8}$ monocyclic or aralkyl;

$R^8$ is alkyl, $C_{3-8}$ monocyclic, aralkyl or aryl;

$R^9$ is hydrogen, alkyl, $C_{3-8}$ monocyclic, aryl or aralkyl;

$R^{10}$ and $R^{11}$ are each independently hydrogen or alkyl or $R^{10}$ and $R^{11}$ together with the N-atoms to which they are attached form an imidazolidin or hexahydropyrimidine ring that is unsubstituted or alkyl-substituted;

X is —CH($R^3$)—;

Z is —N($R^7$)— or oxygen, wherein Y is —CO— when Z is —N($R^7$)— and Y is —CH($R^9$)— when Z is oxygen; and p is zero or 1;

comprising reacting a compound of formula XXXXVI

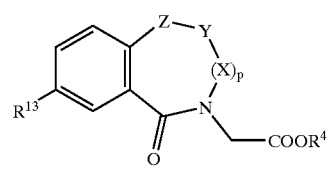

XXXXVI with H$_2$N—CH($R^5$)—CH$_2$—COOR$^4$ under coupling conditions, wherein $R^{13}$ is

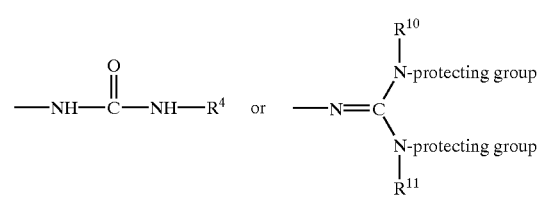

and $R^3$ to $R^{11}$, X, Y, Z, m, n and p are as above and the protecting group is an amino protecting group, to yield the corresponding compound of formula XXXXVIII

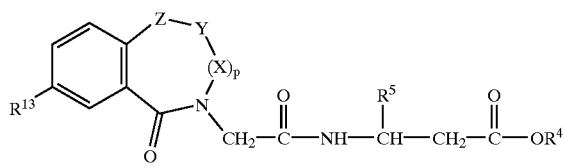

and then treating the compound of formula XXXXVIII to hydrolyze the ester group containing $R^4$ to yield the corresponding carboxylic acid, and when $R^{13}$ is the second group shown above to remove the amino protecting groups, thereby yielding the corresponding compound of formula I.

27. A compound of formula XXXXV

XXXXV

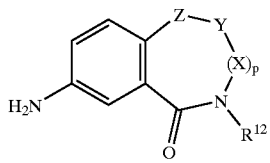

wherein
$R^{12}$ is

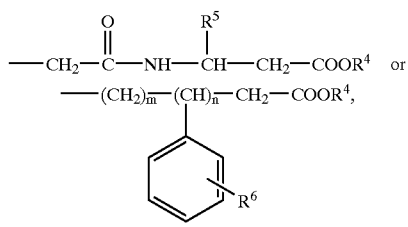

$R^3$ is hydrogen, alkyl, $C_{3-8}$ monocyclic, aralkyl, aryl or carboxyalkyl;
$R^4$ is alkyl or aralkyl;
$R^5$ is hydrogen, alkyl, aryl, saturated, partially unsaturated or aromatic 5- to 10-membered heterocycle that contains one or more hetero atoms selected from nitrogen, oxygen and sulfur, or $R^5$ is —CO—NH—$R^8$;
$R^6$ is hydrogen or

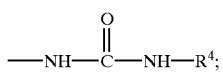

$R^7$ is hydrogen, alkyl, $C_{3-8}$ monocyclic or aralkyl;
$R^8$ is alkyl $C_{3-8}$ monocyclic, aralkyl or aryl;
$R^9$ is hydrogen, alkyl, $C_{3-8}$ monocyclic, aryl or aralkyl;
X is —CH($R^3$)—;
Z is —N($R^7$)— or oxygen, wherein Y is —CO— when Z is —N($R^7$)— and Y is —CH($R^9$)— when Z is oxygen; and m, n and p are zero or whole positive numbers, wherein m is 2 to 5; n is zero or 1; p is zero or 1.

28. The compound according to claim 27, wherein
X is —CH($R^3$)—;
$R^3$ is hydrogen, alkyl, aralkyl, or carboxyalkyl;
$R^{12}$ is

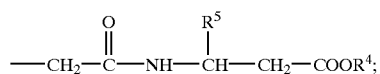

$R^4$ is alkyl; and
$R^5$ is hydrogen, alkyl or aryl.

29. The compound according to claim 28, 3-[2-(7-amino-5-oxo-2,3-dihydro-5H-benzo[f][1,4]oxazepin-4-yl)-acetylamino]-propionic acid ethyl ester.

30. A compound of formula XXXXVI

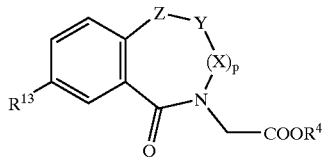

XXXXVI wherein $R^{13}$ is

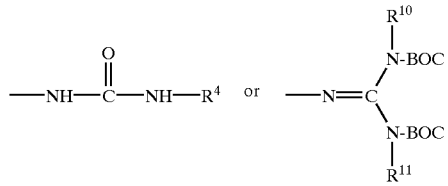

$R^3$ is hydrogen, alkyl, $C_{3-8}$ monocyclic, aralkyl, aryl or carboxyalkyl;
$R^4$ is alkyl or aralkyl;
$R^7$ is hydrogen, alkyl, $C_{3-8}$ monocyclic or aralkyl;
$R^9$ is hydrogen, alkyl, $C_{3-8}$ monocyclic, aryl or aralkyl;
$R^{10}$ and $R^{11}$ are each independently hydrogen or alkyl or $R^{10}$ and $R^{11}$ together with the N-atoms to which they are attached form an imidazolidin or hexahydropyrimidine ring that can be alkyl-substituted;
X is —CH($R^3$)—;
Z is —N($R^7$)— or oxygen, wherein Y is —CO— when Z is —N($R^7$)— and Y is —CH($R^9$)— when Z is oxygen; and
p is zero or 1.

* * * * *

UNITED STATES PATENT AND TRADEMARK OFFICE
CERTIFICATE OF CORRECTION

PATENT NO.    : 6,506,744 B2
DATED         : January 7, 2003
INVENTOR(S)   : Kengo Aritomi et al.

It is certified that error appears in the above-identified patent and that said Letters Patent is hereby corrected as shown below:

<u>Title page,</u>
Item [*] Notice, Patent Adjustment should read -- 0 days. --.

Signed and Sealed this

Twentieth Day of July, 2004

JON W. DUDAS
*Acting Director of the United States Patent and Trademark Office*